(12) United States Patent
Asano

(10) Patent No.: US 11,879,109 B2
(45) Date of Patent: Jan. 23, 2024

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventor: Ayano Asano, Ichihara (JP)

(73) Assignee: RESONAC CORPORATION, Tokyo (JP)

( * ) Notice: Subject to any disclaimer, the term of this patent is extended or adjusted under 35 U.S.C. 154(b) by 1 day.

(21) Appl. No.: 17/760,973

(22) PCT Filed: Sep. 8, 2020

(86) PCT No.: PCT/JP2020/033971
§ 371 (c)(1),
(2) Date: Mar. 16, 2022

(87) PCT Pub. No.: WO2021/054202
PCT Pub. Date: Mar. 25, 2021

(65) Prior Publication Data
US 2022/0372390 A1 Nov. 24, 2022

(30) Foreign Application Priority Data
Sep. 18, 2019 (JP) .................. 2019-169489

(51) Int. Cl.
*C10M 107/38* (2006.01)
*G11B 5/725* (2006.01)
(Continued)

(52) U.S. Cl.
CPC ......... *C10M 107/38* (2013.01); *C08G 65/007* (2013.01); *C10M 107/32* (2013.01);
(Continued)

(58) Field of Classification Search
CPC .... G11B 5/7257; G11B 5/725; C10M 107/38; C10M 107/32; C10M 2213/06;
(Continued)

(56) References Cited

U.S. PATENT DOCUMENTS 4,360,645 A 11/1982 Krespan et al.
4,526,833 A 7/1985 Burguette et al.
(Continued)

FOREIGN PATENT DOCUMENTS

CN 1705698 A 12/2005
CN 101121908 A 2/2008
(Continued)

OTHER PUBLICATIONS

English abstract of WO-2019039200-A1, Daisuke, Feb. 2019, p. 1-4.*
(Continued)

*Primary Examiner* — Holly Rickman
(74) *Attorney, Agent, or Firm* — Sughrue Mion, PLLC

(57) ABSTRACT

A fluorine-containing ether compound represented by the following formula (1).

$$R^1-R^2-CH_2-R^3-CH_2-R^4 \quad (1)$$

($R^1$ is an organic group having an alicyclic structure having 3 to 13 carbon atoms; $R^2$ is represented by the following formula (2), and a in the formula (2) is an integer of 1 to 3; $R^3$ is a perfluoropolyether chain; and $R^4$ is a terminal group having two or three polar groups, in which individual polar groups bond to different carbon atoms and the carbon atoms to which the polar groups bond are bonded to each other through a linking group having a carbon atom to which the polar groups do not bond.)

(Continued)

US 11,879,109 B2

Page 2

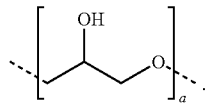

(2)

14 Claims, 1 Drawing Sheet

(51) Int. Cl.
 *C08G 65/00* (2006.01)
 *C10M 107/32* (2006.01)
 *C10N 40/18* (2006.01)
(52) U.S. Cl.
 CPC ........ *G11B 5/7257* (2020.08); *C08G 2650/04* (2013.01); *C08G 2650/48* (2013.01); *C10M 2213/0606* (2013.01); *C10N 2040/18* (2013.01)
(58) Field of Classification Search
 CPC ....... C10M 2213/0606; C10N 2040/18; C08G 65/007; C08G 2050/04; C08G 2050/48
 See application file for complete search history.

(56) References Cited

U.S. PATENT DOCUMENTS

| | | |
|---|---|---|
| 5,157,066 A | 10/1992 | Shoji et al. |
| 5,221,494 A | 6/1993 | Ikeda et al. |
| 5,959,058 A | 9/1999 | Tonelli et al. |
| 6,323,163 B1 | 11/2001 | Sasaki et al. |
| 10,803,898 B2 | 10/2020 | Fukumoto et al. |
| 11,011,200 B2 | 5/2021 | Uetake et al. |
| 11,220,649 B2 | 1/2022 | Fukumoto et al. |
| 11,225,624 B2 | 1/2022 | Kato et al. |
| 11,261,394 B2 | 3/2022 | Kato et al. |
| 11,279,664 B2 | 3/2022 | Yagyu et al. |
| 11,427,779 B2 | 8/2022 | Yamaguchi et al. |
| 11,639,330 B2 * | 5/2023 | Nanko .................. C07C 255/19 428/848 |
| 2004/0235685 A1 | 11/2004 | Russo et al. |
| 2005/0123855 A1 | 6/2005 | Hegel |
| 2005/0197408 A1 | 9/2005 | Shirakawa et al. |
| 2006/0111251 A1 | 5/2006 | Tonelli et al. |
| 2009/0281250 A1 | 11/2009 | Desimone et al. |
| 2010/0233513 A1 | 9/2010 | Imai et al. |
| 2010/0261039 A1 | 10/2010 | Itoh et al. |
| 2012/0008228 A1 | 1/2012 | Mabuchi et al. |
| 2012/0225217 A1 | 9/2012 | Itoh et al. |
| 2013/0209837 A1 | 8/2013 | Sagata et al. |
| 2015/0274960 A1 | 10/2015 | Fukuda et al. |
| 2015/0371672 A1 | 12/2015 | Sagata |
| 2016/0068778 A1 | 3/2016 | Conley et al. |
| 2016/0203839 A1 | 7/2016 | Shimizu |
| 2017/0152456 A1 | 6/2017 | Sagata et al. |
| 2017/0260472 A1 | 9/2017 | Sagata et al. |
| 2017/0331155 A1 | 11/2017 | Yang et al. |
| 2018/0009773 A1 | 1/2018 | Uetake et al. |
| 2018/0022851 A1 | 1/2018 | Takao et al. |
| 2018/0047419 A1 | 2/2018 | Fukumoto et al. |
| 2018/0127543 A1 | 5/2018 | Watanabe et al. |
| 2019/0084911 A1 | 3/2019 | Yagyu et al. |
| 2019/0185621 A1 | 6/2019 | Naitou et al. |
| 2019/0352573 A1 | 11/2019 | Hatta et al. |
| 2019/0382675 A1 | 12/2019 | Fukumoto et al. |
| 2019/0382676 A1 | 12/2019 | Yamaguchi et al. |
| 2020/0010619 A1 | 1/2020 | Minami et al. |
| 2021/0062101 A1 | 3/2021 | Kato et al. |
| 2021/0062102 A1 | 3/2021 | Kato et al. |
| 2021/0155751 A1 | 5/2021 | Kato |
| 2021/0188766 A1 | 6/2021 | Nanko et al. |
| 2022/0169941 A1 | 6/2022 | Shibata |
| 2022/0372390 A1 | 11/2022 | Asano |
| 2023/0090239 A1 | 3/2023 | Nanko |

FOREIGN PATENT DOCUMENTS

| | | |
|---|---|---|
| CN | 102639477 A | 8/2012 |
| CN | 114599631 A | 6/2022 |
| EP | 1 479 753 A2 | 11/2004 |
| EP | 3 081 549 A1 | 10/2016 |
| JP | 57-176973 A | 10/1982 |
| JP | 61-126052 A | 6/1986 |
| JP | 3-7798 A | 1/1991 |
| JP | 5-12655 A | 1/1993 |
| JP | 2866622 B2 | 3/1993 |
| JP | 8-259882 A | 10/1996 |
| JP | 10-106822 A | 4/1998 |
| JP | 11-60720 A | 3/1999 |
| JP | 11-71440 A | 3/1999 |
| JP | 11-131083 A | 5/1999 |
| JP | 2000-264883 A | 9/2000 |
| JP | 2001-134924 A | 5/2001 |
| JP | 2001-209924 A | 8/2001 |
| JP | 2002-69037 A | 3/2002 |
| JP | 2004-115640 A | 4/2004 |
| JP | 2004-346318 A | 12/2004 |
| JP | 2006-131874 A | 5/2006 |
| JP | 2009-266360 A | 11/2009 |
| JP | 2010-143855 A | 7/2010 |
| JP | 2010-241831 A | 10/2010 |
| JP | 2010-282707 A | 12/2010 |
| JP | 4632144 B2 | 2/2011 |
| JP | 2012-9090 A | 1/2012 |
| JP | 2012-33253 A | 2/2012 |
| JP | 2013-163667 A | 8/2013 |
| JP | 2013-181014 A | 9/2013 |
| JP | 2013-181140 A | 9/2013 |
| JP | 2014-509677 A | 4/2014 |
| JP | 5465454 B2 | 4/2014 |
| JP | 5613916 B2 | 10/2014 |
| JP | 5909837 B2 | 4/2016 |
| JP | 6122191 B1 | 4/2017 |
| JP | 2018-2673 A | 1/2018 |
| JP | 2018-24614 A | 2/2018 |
| JP | 2018-035348 A | 3/2018 |
| JP | 2018-076404 A | 5/2018 |
| JP | 2018-521183 A | 8/2018 |
| WO | 98/17617 A1 | 4/1998 |
| WO | 2006/011387 A1 | 2/2006 |
| WO | 2009/035075 A1 | 3/2009 |
| WO | 2009/123043 A1 | 10/2009 |
| WO | 2011/099131 A1 | 8/2011 |
| WO | 2012/170009 A2 | 12/2012 |
| WO | 2015/087615 A1 | 6/2015 |
| WO | 2015/199037 A1 | 12/2015 |
| WO | 2016/084781 A1 | 6/2016 |
| WO | 2017/005834 A1 | 1/2017 |
| WO | 2017/145995 A1 | 8/2017 |
| WO | 2017/154403 A1 | 9/2017 |
| WO | 2018/116742 A1 | 6/2018 |
| WO | 2018/139058 A1 | 8/2018 |
| WO | 2018/139174 A1 | 8/2018 |
| WO | 2018/147017 A1 | 8/2018 |
| WO | 2018/159232 A1 | 9/2018 |
| WO | 2019/039200 A1 | 2/2019 |
| WO | 2019/049585 A1 | 3/2019 |
| WO | 2019/054148 A1 | 3/2019 |
| WO | 2019/087548 A1 | 5/2019 |

OTHER PUBLICATIONS

International Search Report for PCT/JP2020/033971 dated Nov. 24, 2020 [PCT/ISA/210].
International Search Report for PCT/JP2020/041613, dated Dec. 28, 2020.
Office Action dated May 24, 2023 in U.S. Appl. No. 17/772,043.

(56) References Cited

OTHER PUBLICATIONS

"Cihai Sciences vol. 1" Edited by Cihai Editorial Committee, Shanghai Lexicographical Publishing House, Aug. 30, 1980, p. 329 (3 pages total).
Advisory Action dated Aug. 11, 2021, issued in U.S. Appl. No. 16/480,464.
Communication dated Dec. 24, 2019, from the Japanese Patent Office in Application No. 2016-133653.
International Search Report for PCT/JP2017/003165 dated May 9, 2017.
International Search Report for PCT/JP2017/043451 dated Feb. 27, 2018 [PCT/ISA/210].
International Search Report for PCT/JP2018/000071 dated Mar. 6, 2018 [PCT/ISA/210].
International Search Report for PCT/JP2018/031161, dated Nov. 27, 2018 (PCT/ISA/210).
International Search Report for PCT/JP2019/033697 dated Nov. 5, 2019.
International Search Report for PCT/JP2019/033700 dated Nov. 12, 2019 [PCT/ISA/210].
International Search Report for PCT/JP2021/003708 dated Mar. 23, 2021.
International Search Report of PCT/JP2020/010759 dated May 26, 2020 [PCT/ISA/210].
Notice of Allowance dated Sep. 10, 2021 issued in U.S. Appl. No. 16/480,464.
Notice of Allowance dated Feb. 8, 2021 from the US Patent & Trademark Office in U.S. Appl. No. 15/640,729.
Notice of Allowance dated Nov. 16, 2021 from the US & Patent & Trademark Office in U.S. Appl. No. 16/082,349.
Notice of Allowance dated Feb. 9, 2023 in U.S. Appl. No. 17/274,702.
Notice of Allowance dated May 5, 2022 in U.S. Appl. No. 16/480,483.
Notice of Allowance dated Nov. 9, 2021 in U.S. Appl. No. 16/644,586.
Office Action dated Dec. 2, 2020 from the China National Intellectual Property Administration in CN Application No. 201780012469.9.
Restriction Requirement dated Jun. 10, 2019 from the US & Patent & Trademark Office in U.S. Appl. No. 15/640,729.
Office Action dated Jun. 8, 2021 from the US & Patent & Trademark Office in U.S. Appl. No. 16/082,349.
Office Action dated Mar. 11, 2021 from the China National Intellectual Property Administration in CN Application No. 201780070908.1.
Supplemental Notice of Allowance dated Mar. 4, 2021 from the US & Patent & Trademark Office in U.S. Appl. No. 15/640,729.
Office Action dated May 13, 2020 from the US & Patent & Trademark Office in U.S. Appl. No. 15/640,729.
Office Action dated May 25, 2021 from the China National Intellectual Property Administration in CN Application No. 201780012469.9.
Office Action dated Nov. 12, 2020 from the US & Patent & Trademark Office in U.S. Appl. No. 15/640,729.
Office Action dated Oct. 29, 2019 from the US & Patent & Trademark Office in U.S. Appl. No. 15/640,729.
Office Action Final dated Apr. 16, 2021 Issued in U.S. Appl. No. 16/480,464.
Office Action dated Dec. 21, 2022 in U.S. Appl. No. 17/274,466.
Office Action dated Jan. 19, 2022 in U.S. Appl. No. 16/480,483.
Office Action dated Jan. 19, 2023 in U.S. Appl. No. 17/437,251.
Office Action dated Jul. 23, 2021 in U.S. Appl. No. 16/644,586.
Office Action dated Jun. 21, 2021 in U.S. Appl. No. 16/480,483.
Office Action dated Oct. 25, 2022 in U.S. Appl. No. 17/274,702.
Office Action Non-Final dated Jan. 28, 2021, issued in U.S. Appl. No. 16/480,464.
Restriction Election Requirement dated Nov. 23, 2020, issued in U.S. Appl. No. 16/480,464.
Office Action dated Jun. 7, 2023 in U.S. Appl. No. 17/797,177.
Supplemental Notice of Allowance dated Dec. 2, 2021 in U.S. Appl. No. 16/644,586.
Non-Final Office Action dated Apr. 26, 2023 in U.S. Appl. No. 17/788,075.
R.J. Waltman, "Z-Tetraol composition and bonding to the underlying carbon surface", Journal of Colloid and Interface Science, 2009, vol. 333, pp. 540-547 (8 pages total).
International Search Report for PCT/JP2020/047987, dated Feb. 16, 2021.
International Search Report of PCT/JP2018/028455 dated Oct. 2, 2018.
Final Office Action dated May 7, 2022 issued by the Chinese Patent Office in Chinese Application No. 201880053594.9.
Non-Final Office Action dated Sep. 15, 2022 in U.S. Appl. No. 16/640,132.
Notice of Allowance dated Jan. 5, 2023, in U.S. Appl. No. 16/640,132.

\* cited by examiner

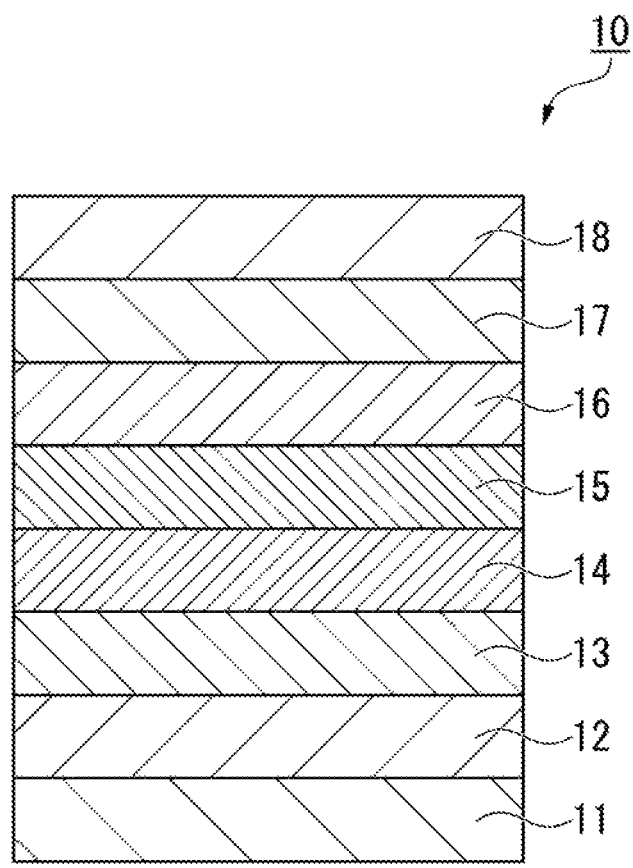

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATION

This application is a National Stage of International Application No. PCT/JP2020/033971 filed Sep. 8, 2020, claiming priority based on Japanese Patent Application No. 2019-169489 filed Sep. 18, 2019.

TECHNICAL FIELD

The present invention relates to a fluorine-containing ether compound, a lubricant for a magnetic recording medium, and a magnetic recording medium.

Priority is claimed on Japanese Patent Application No. 2019-169489, filed Sep. 18, 2019, the content of which is incorporated herein by reference.

BACKGROUND ART

Development of magnetic recording media suitable for high recording densities is underway to improve the recording densities of magnetic recording/reproducing devices.

As a conventional magnetic recording medium, there is a magnetic recording medium in which a recording layer is formed on a substrate and a protective layer made of carbon or the like is formed on the recording layer. The protective layer protects information recorded in the recording layer and enhances the slidability of a magnetic head. However, sufficient durability of the magnetic recording medium cannot be obtained by simply providing the protective layer on the recording layer. Therefore, it is usual to apply a lubricant to the surface of the protective layer to form a lubricating layer.

As a lubricant that is used at the time of forming a lubricating layer in a magnetic recording medium, for example, there is a fluorine-based polymer having a repeating structure containing $CF_2$. As the fluorine-based polymer, a polymer has been proposed wherein compounds having a polar group such as a hydroxy group at a terminal thereof are bonded by an aromatic ring and/or saturated alicyclic structure.

Patent Document 1 discloses a composition comprising a central core selected from the group consisting of triazine, benzene, diphenyl ether, polyphenyl ether, a cyclohydrocarbon and derivatives thereof and one or more arms extending from the central core. Patent Document 1 discloses that the one or more arms comprise a perfluoropolyether or a perfluoropolyether derivative.

Patent Document 2 discloses a fluorine-containing ether compound in which three fluorine-containing ether groups having a polar group at the end thereof are connected to a trivalent atom or a trivalent atom group.

CITATION LIST

Patent Documents

[Patent Document 1]
Published Japanese translation of No. 2014-509677 of PCT International Publication
[Patent Document 2]
PCT International Publication No. WO 2018/159232

SUMMARY OF INVENTION

Technical Problem

There is a demand for a further decrease in the flying height of a magnetic head in magnetic recording/reproducing devices. This requires a further decrease in the thickness of a lubricating layer in magnetic recording media.

However, usually, there is a tendency that a decrease in the thickness of a lubricating layer degrades the coatability of the lubricating layer and thereby degrades the chemical substance resistance of magnetic recording media. In addition, when the thickness of a lubricating layer is made thinner, adhesion between a protective layer and the lubricating layer which coats the surface of the protective layer is decreased and pickup, which is the adhesion of a fluorine-containing ether compound included in a lubricating layer to a magnetic head, tends to occur.

In addition, a magnetic recording/reproducing device is generally included in a housing provided in a personal computer. As the result, there is a case that such a magnetic recording/reproducing device is locally exposed to a high-temperature environment. Therefore, a layer having excellent heat stability (heat resistance) is requested as a lubricating layer of the magnetic recording/reproducing device.

The present invention has been made in consideration of the aforementioned circumstances, and an objective of the present invention is to provide a fluorine-containing ether compound capable of forming a lubricating layer which has excellent chemical substance resistance and heat resistance and can prevent pickup in spite of a thin thickness, and capable of being preferably used as a material of lubricants for a magnetic recording media.

In addition, an objective of the present invention is to provide a lubricant for a magnetic recording medium that contains the fluorine-containing ether compound of the present invention.

In addition, an objective of the present invention is to provide a magnetic recording medium having a lubricating layer containing the fluorine-containing ether compound of the present invention and having excellent reliability and durability.

Solution to Problem

The present inventor repeated intensive studies to solve the aforementioned problems.

As a result, the present inventor found that the above problems can be solved by using a fluorine-containing ether compound, wherein an organic group having an alicyclic structure having 3 to 13 carbon atoms is provided at a first end portion of a perfluoropolyether chain through a specific linking group and a methylene group, and a specific end group having two or three polar groups is provided at a second end portion of the perfluoropolyether chain through a methylene group, and conceived the present invention.

That is, a first aspect of the present invention is the following fluorine-containing ether compound.

[1] A fluorine-containing ether compound represented by the following formula (1).

$$R^1-R^2-CH_2-R^3-CH_2-R^4 \qquad (1)$$

(In the formula (1), $R^1$ is an organic group having an alicyclic structure having 3 to 13 carbon atoms; $R^2$ is represented by the following formula (2), and a in the formula (2) is an integer of 1 to 3; $R^3$ is a perfluoropolyether chain; and $R^4$ is a terminal group having two or three polar groups, in which individual polar groups bond to different carbon atoms and the carbon atoms to which the polar groups bond are bonded to each other through a linking group having a carbon atom to which the polar groups do not bond.)

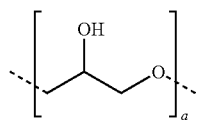
(2)

The fluorine-containing ether compound of the first aspect of the present invention may preferably have the following characteristics as described below. Two or more of the following characteristics may be preferably combined together.

[2] The fluorine-containing ether compound according to [1], in which the alicyclic structure of $R^1$ is a saturated alicyclic structure.

[3] The fluorine-containing ether compound according to [1] or [2], in which the alicyclic structure of $R^1$ is one selected from the group consisting of cyclopropane, cyclobutane, cyclopentane, cyclohexane, cycloheptane, cyclooctane, cyclononane, cyclodecane, cycloundecane, cyclododecane, cyclotridecane and adamantane.

[4] The fluorine-containing ether compound according to any one of [1] to [3], in which any one of a carbon atom, an oxygen atom and a nitrogen atom included in $R^1$ is bonded to a carbon atom included in $R^2$.

[5] The fluorine-containing ether compound according to any one of [1] to [4], in which the alicyclic structure of $R^1$ has a substituent, which is selected from a functional group selected from the group consisting of a hydroxyl group, an alkoxy group, an amide group, an amino group, a carbonyl group, a carboxyl group, a nitro group, a cyano group and a sulfo group, or an alkyl group having the functional group.

[6] The fluorine-containing ether compound according to any one of [1] to [5], in which $R^3$ is any of the following formulae (3) to (5).

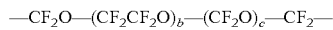  (3)

(b and c in the formula (3) indicate average degrees of polymerization and each independently represents 0 to 30. Here, there is no case where b and c become 0 at the same time.)

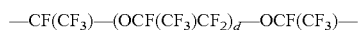  (4)

(d in the formula (4) indicates an average degree of polymerization and represents 0.1 to 30.)

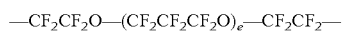  (5)

(e in the formula (5) indicates an average degree of polymerization and represents 0.1 to 30.)

[7] The fluorine-containing ether compound according to any one of [1] to [6], in which the polar group in $R^4$ is a hydroxyl group.

[8] The fluorine-containing ether compound according to any one of [1] to [7], in which $R^4$ is a terminal group which is any of the following formulae (6) to (9).

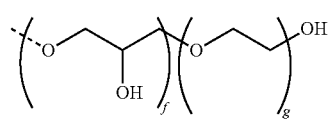 (6)

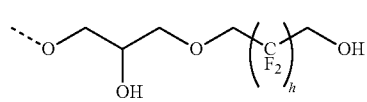 (7)

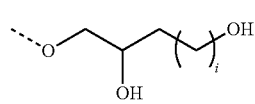 (8)

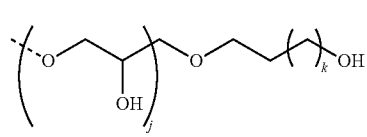 (9)

(In the formula (6), f represents an integer of 1 or 2, and g represents an integer of 1 to 5.)

(In the formula (7), h represents an integer of 2 to 5.)

(In the formula (8), i represents an integer of 1 to 5.)

(In the formula (9), j represents an integer of 1 or 2, and k represents an integer of 1 or 2.)

[9] The fluorine-containing ether compound according to any one of [1] to [8], in which a number-average molecular weight thereof is within a range of 500 to 10000.

[10] The fluorine-containing ether compound according to any one of [1] to [9], in which the compound represented by the formula (1) is any of compounds represented by the following formulae (A) to (C), and (G) to (O).

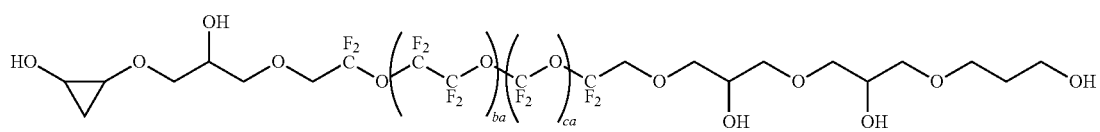 (A)

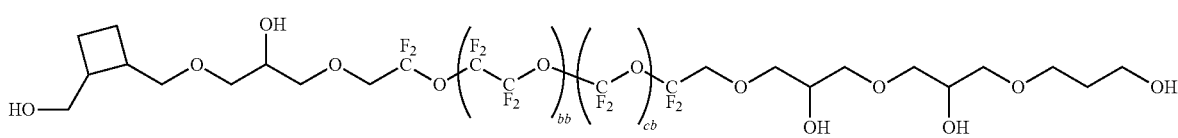 (B)

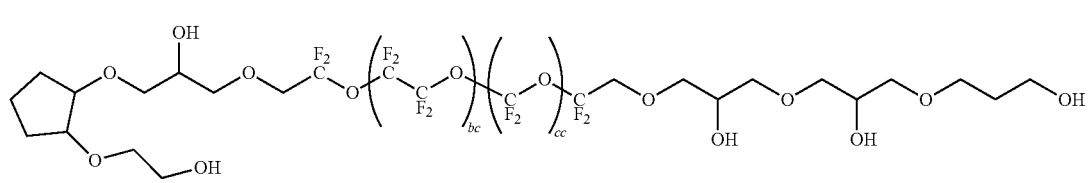 (C)

(In the formula (A), ba and ca indicate average degrees of polymerization, ba represents 0 to 30, and ca represents 0 to 30. Here, there is no case where ba and ca become 0 at the same time.)

(In the formula (B), bb and cb indicate average degrees of polymerization, bb represents 0 to 30, and cb represents 0 to 30. Here, there is no case where bb and cb become 0 at the same time.)

(In the formula (C), bc and cc indicate average degrees of polymerization, bc represents 0 to 30, and cc represents 0 to 30. Here, there is no case where bc and cc become 0 at the same time.)

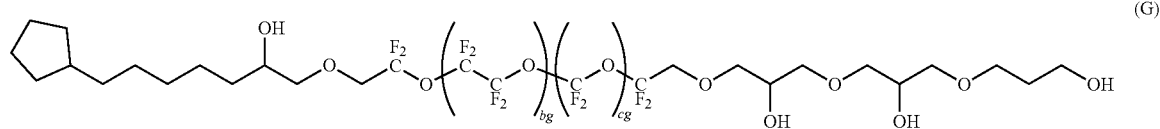

(G)

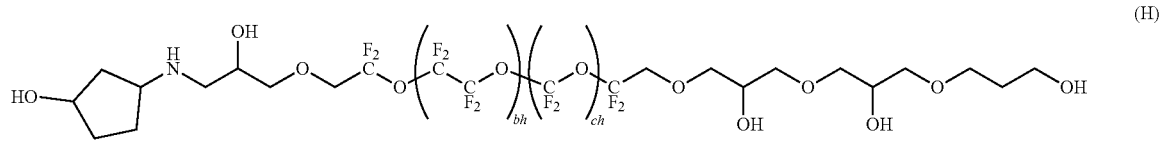

(H)

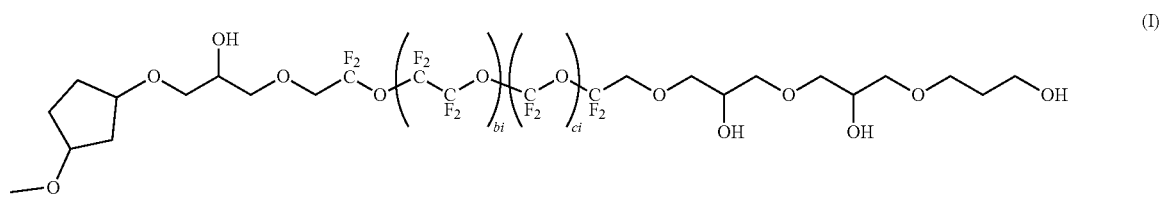

(I)

(In the formula (G), bg and cg indicate average degrees of polymerization, bg represents 0 to 30, and cg represents 0 to 30. Here, there is no case where bg and cg become 0 at the same time.)

(In the formula (H), bh and ch indicate average degrees of polymerization, bh represents 0 to 30, and ch represents 0 to 30. Here, there is no case where bh and ch become 0 at the same time.)

(In the formula (I), bi and ci indicate average degrees of polymerization, bi represents 0 to 30, and ci represents 0 to 30. Here, there is no case where bi and ci become 0 at the same time.)

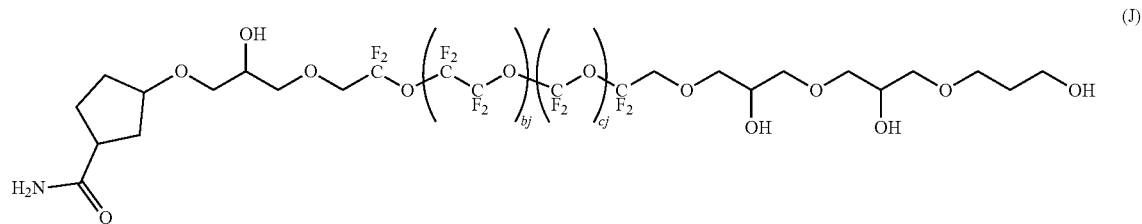

(J)

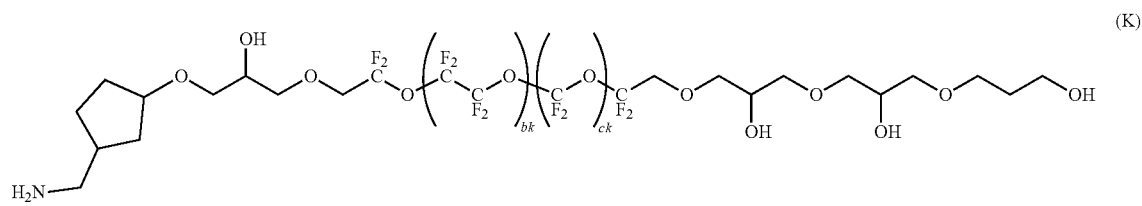

(K)

(In the formula (J), bj and cj indicate average degrees of polymerization, bj represents 0 to 30, and cj represents 0 to 30. Here, there is no case where bj and cj become 0 at the same time.)

(In the formula (K), bk and ck indicate average degrees of polymerization, bk represents 0 to 30, and ck represents 0 to 30. Here, there is no case where bk and ck become 0 at the same time.)

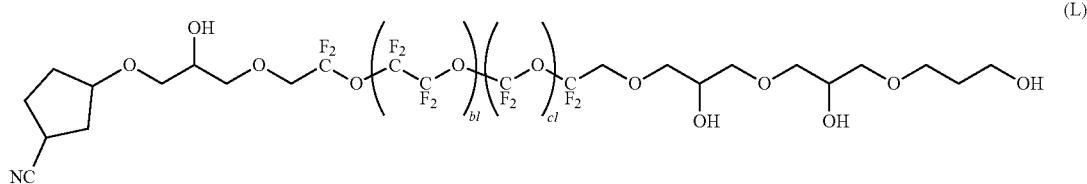

(L)

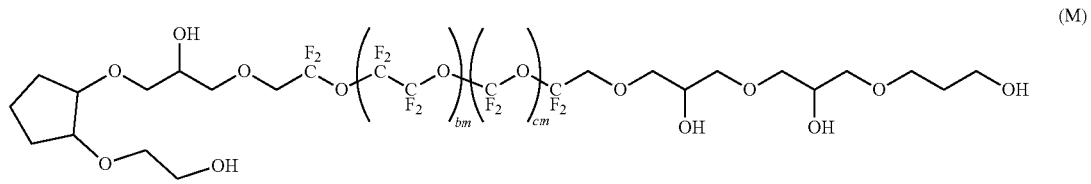

(M)

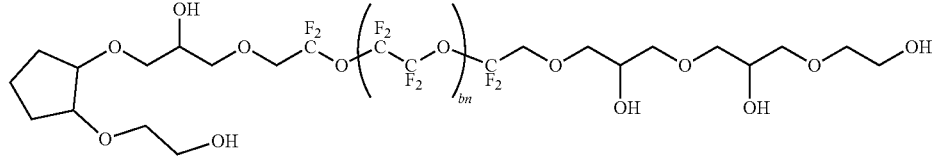

(N)

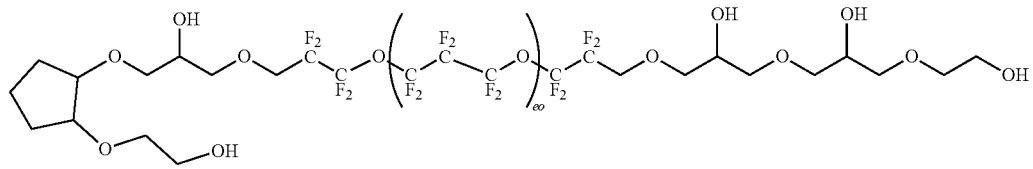

(O)

(In the formula (L), bl and cl indicate average degrees of polymerization, bl represents 0 to 30, and cl represents 0 to 30. Here, there is no case where bl and cl become 0 at the same time.)

(In the formula (M), bm and cm indicate average degrees of polymerization, bm represents 0 to 30, and cm represents 0 to 30. Here, there is no case where bm and cm become 0 at the same time.)

(In the formula (N), bn indicates an average degree of polymerization, and bn represents 0.1 to 30.)

(In the formula (O), eo indicates an average degree of polymerization, and eo represents 0.1 to 30.)

[11] The fluorine-containing ether compound according to any one of [1] to [9], in which the compound represented by the formula (1) is any of compounds represented by the following formulae (T) to (X).

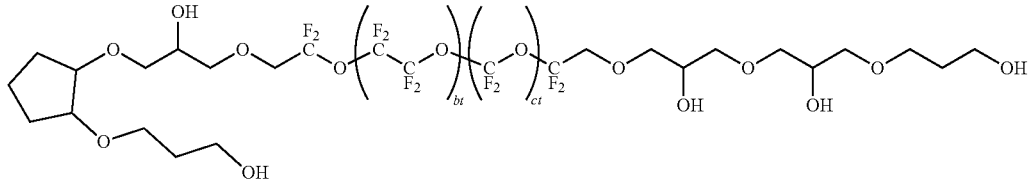

(T)

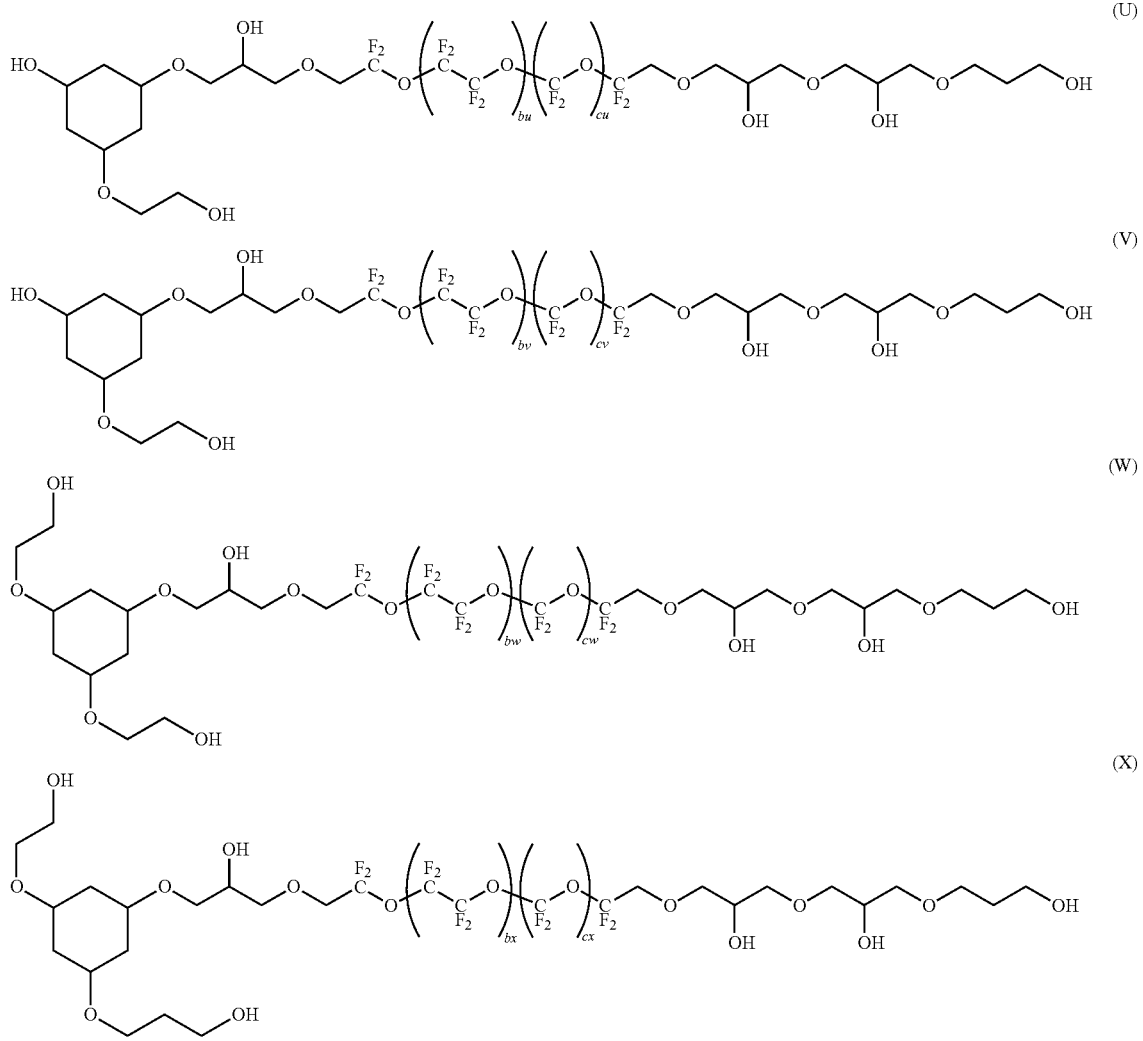

(In the formula (T), bt and ct indicate average degrees of polymerization, bt represents 0 to 30, and ct represents 0 to 30. Here, there is no case where bt and ct become 0 at the same time.)

(In the formula (U), bu and cu indicate average degrees of polymerization, bu represents 0 to 30, and cu represents 0 to 30. Here, there is no case where bu and cu become 0 at the same time.)

(In the formula (V), by and cv indicate average degrees of polymerization, by represents 0 to 30, and cv represents 0 to 30. Here, there is no case where by and cv become 0 at the same time.)

(In the formula (W), bw and cw indicate average degrees of polymerization, bw represents 0 to 30, and cw represents 0 to 30. Here, there is no case where bw and cw become 0 at the same time.)

(In the formula (X), bx and cx indicate average degrees of polymerization, bx represents 0 to 30, and cx represents 0 to 30. Here, there is no case where bx and cx become 0 at the same time.)

[12] A lubricant for a magnetic recording medium containing the fluorine-containing ether compound according to any one of [1] to [11].

[13] A magnetic recording medium having at least a magnetic layer, a protective layer, and a lubricating layer sequentially provided on a substrate, in which the lubricating layer contains the fluorine-containing ether compound according to any one of [1] to [11].

[14] The magnetic recording medium according to [13], in which the lubricating layer has an average film thickness of 0.5 nm to 2 nm.

Advantageous Effects of Invention

The fluorine-containing ether compound of the present invention is a compound represented by the formula (1) and is preferable as a material for lubricants for magnetic recording media.

The lubricant for a magnetic recording medium of the present invention contains the fluorine-containing ether compound of the present invention and is thus capable of forming a lubricating layer that has excellent chemical substance resistance and heat resistance and can suppress pickup in spite of a thin thickness.

The magnetic recording medium of the present invention is provided with a lubricating layer that has excellent chemical substance resistance and heat resistance and can suppress pickup, and thus has excellent reliability and durability.

BRIEF DESCRIPTION OF DRAWINGS

FIG. 1 is a schematic cross-sectional view showing an embodiment of a magnetic recording medium of the present invention.

DESCRIPTION OF EMBODIMENTS

Hereinafter, a fluorine-containing ether compound, a lubricant for a magnetic recording medium (hereinafter, may be abbreviated as "lubricant" in some cases) and a magnetic recording medium of the present invention will be described in detail. The present invention is not limited only to an embodiment to be described below.
[Fluorine-Containing Ether Compound]

A fluorine-containing ether compound of the present embodiment is represented by the following formula (1).

(In the formula (1), $R^1$ is an organic group having an alicyclic structure having 3 to 13 carbon atoms. $R^2$ is represented by the following formula (2). a in the formula (2) is an integer of 1 to 3. $R^3$ is a perfluoropolyether chain. $R^4$ is a terminal group having two or three polar groups, in which individual polar groups bond to different carbon atoms and the carbon atoms to which the polar groups bond are bonded to each other through a linking group having a carbon atom to which the polar groups do not bond.)

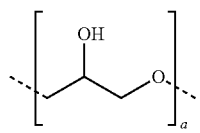

Here, the reason why a lubricating layer that has excellent chemical substance resistance and heat resistance and can suppress pickup in spite of a thin thickness can be obtained in a case where the lubricating layer is formed on a protective layer of a magnetic recording medium using a lubricant containing the fluorine-containing ether compound of the present embodiment will be described below.

As shown in the formula (1), the fluorine-containing ether compound of the present embodiment has a perfluoropolyether chain represented by $R^3$ (hereinafter, may be abbreviated as "PFPE chain" in some cases). The PFPE chain coats the surface of a protective layer and imparts lubricity to a lubricating layer to reduce a friction force between a magnetic head and the protective layer, when the lubricating layer is formed by applying a lubricant containing the fluorine-containing ether compound onto the protective layer.

As shown in the formula (1), an organic group ($R^1$) having an alicyclic structure having 3 to 13 carbon atoms is provided at a first end portion of a PFPE chain, which is represented by $R^3$, through a linking group ($R^2$) represented by the formula (2) and a methylene group (—$CH_2$—).

In the fluorine-containing ether compound represented by the formula (1), an alicyclic structure having 3 to 13 carbon atoms which is included in the organic group represented by $R^1$ has heat stability. Accordingly, an organic group represented by $R^1$ contributes to improve heat resistance of a lubricating layer which includes the fluorine-containing ether compound of the embodiment. Accordingly, when a lubricant containing the fluorine-containing ether compound shown by the formula (1) is used, a lubricating layer which has excellent heat resistance can be obtained.

In the fluorine-containing ether compound shown by the formula (1), a linking group ($R^2$) represented by the formula (2) is disposed between the organic group represented by $R^1$ and the PFPE chain shown by $R^3$. The linking group ($R^2$) represented by the formula (2) includes one to three hydroxyl groups (—OH). Due to this fact, a lubricating layer containing the fluorine-containing ether compound of the present embodiment can have excellent adherence (adhesion) to the protective layer. In addition, the linking group ($R^2$) represented by the formula (2) includes an ether bond (—O—) and thus imparts appropriate flexibility to the molecular structure of the fluorine-containing ether compound represented by the formula (1). Due to these facts, the fluorine-containing ether compound of the present embodiment can make a lubricating layer containing the fluorine-containing ether compound easily adsorbed to a protective layer and provide excellent adhesion between the lubricating layer and the protective layer, compared with, for example, fluorine-containing ether compounds in which an organic group represented by $R^1$ and a PFPE chain represented by $R^3$ directly bond to each other.

As shown in the formula (1), a terminal group represented by $R^4$ having two or three polar groups is placed at a terminal (second end portion) of the PFPE chain represented by $R^3$, wherein the terminal is located on the opposite side of $R^2$, through a methylene group (—$CH_2$—). The terminal group represented by $R^4$ contributes to impart adhesion between a protective layer to which a lubricant containing the fluorine-containing ether compound of the present embodiment is applied and a lubricating layer formed by applying the lubricant. In the lubricating layer containing the fluorine-containing ether compound of the present embodiment, two or three polar groups in the terminal group represented by $R^4$ closely attach the protective layer and the fluorine-containing ether compound, and thereby suppress pickup.

In addition, two or three polar groups included in the terminal group represented by $R^4$ bond to different carbon atoms and the carbon atoms to which the polar groups bond are bonded to each other through a linking group having a carbon atom to which the polar groups do not bond. Accordingly, with respect to the two or three polar groups in $R^4$, the distance between the polar groups is appropriate. As the result, the fluorine-containing ether compound having the terminal group represented by $R^4$ is less likely to be aggregated compared with, for example, fluorine-containing ether compounds in which at least a part of carbon atoms to which polar groups bond in the terminal group represented by $R^4$ are bonded to each other. Therefore, in a lubricating layer containing the fluorine-containing ether compound represented by formula (1), it is possible to prevent the fluorine-containing ether compound which exists without being attached (adsorbed) to a protective layer from being aggregated and attached to a magnetic head as foreign matter (smear), and pickup is suppressed. In addition, since the fluorine-containing ether compounds are less likely to be aggregated, the fluorine-containing ether compound in the lubricating layer is likely to be disposed in a state of spreading and extending uniformly in the plane direction on the protective layer. Therefore, a lubricant containing the fluorine-containing ether compound of the present embodiment is capable of coating the surface of the protective layer at a high coating rate in spite of a thin thickness thereof and capable of forming a lubricating layer having excellent chemical substance resistance. Therefore, the lubricant containing the fluorine-containing ether compound of the present embodiment can contribute to reduction in thickness of the lubricating layer (reduction in magnetic spacing).

In this way, it is assumed that a lubricant containing the fluorine-containing ether compound of the present embodiment is capable of coating the surface of the protective layer at a high coating rate in spite of a thin thickness thereof and capable of forming a lubricating layer which has excellent chemical substance resistance and heat resistance and can suppress pick up.

(Organic Group Represented by $R^1$)

In the fluorine-containing ether compound represented by the formula (1) of the present embodiment, an organic group represented by $R^1$ has an alicyclic structure having 3 to 13 carbon atoms. The alicyclic structure having 3 to 13 carbon atoms is preferably a saturated alicyclic structure, in order to provide a fluorine-containing ether compound which can form a lubricating layer which has more excellent heat resistance. Examples of the alicyclic structure having 3 to 13 carbon atoms include cyclopropane, cyclobutane, cyclopentane, cyclohexane, cycloheptane, cyclooctane, cyclononane, cyclodecane, cycloundecane, cyclododecane, cyclotridecane, adamantane, and the like. As the alicyclic structure having 3 to 13 carbon atoms of the organic group represented by $R^1$, among the compounds described above, a saturated alicyclic structure having 3 to 9 carbon atoms or adamantane, which has good heat stability, is particularly preferable as it is possible to provide a fluorine-containing ether compound which can form a lubricating layer which has more excellent heat resistance.

The number of the alicyclic structure having 3 to 13 carbon atoms included in the organic group represented by $R^1$ may be one, or may be plural. When the number of the alicyclic structure having 3 to 13 carbon atoms included in the organic group represented by $R^1$ is more than one, some of or all of the alicyclic structures may be same or different from each other. The number of the alicyclic structure having 3 to 13 carbon atoms included in the organic group represented by $R^1$ is preferably one, as the fluorine-containing ether compounds are less likely to be aggregated.

The alicyclic structure having 3 to 13 carbon atoms included in the organic group represented by $R^1$ may have one substituent or two or more substituents. When the alicyclic structure has two or more substituents, some of or all of the two or more substituents may be same or different from each other. When the alicyclic structure having 3 to 13 carbon atoms has a substituent, the number of the substituent can be appropriately determined depending on the types of the alicyclic structure having 3 to 13 carbon atoms, and is not particularly limited.

In a case where the alicyclic structure having 3 to 13 carbon atoms has a substituent, a substituent having 0 to 10 carbon atoms is preferable as the substituent. The number of the carbon atom thereof may be 1 to 8 or 2 to 6 as necessary. When the number of the carbon atom of the substituent is 0 to 10, the adsorption of the lubricating layer to a protective layer is not inhibited by a steric hindrance caused by a substituent which has too many carbon atoms, and a lubricating layer having excellent coatability can be obtained, and therefore, such a number is preferable. The number of the carbon atom of the substituent is more preferably 0 to 5, and still more preferably 0 to 2.

In a case where the alicyclic structure having 3 to 13 carbon atoms included in the organic group represented by 1V has a substituent, specific examples of the substituent include at least one functional group which is selected from the group consisting of a hydroxyl group, an alkoxy group, an amide group, an amino group, a carbonyl group, a carboxyl group, a nitro group, a cyano group and a sulfo group, and an alkyl group having the aforementioned functional group. In the alkyl group having the aforementioned functional group, the number of the carbon atom of the alkyl group is preferably 1 to 3, and more preferably 1 or 2.

Among the substituents, a hydroxyl group, an alkoxy group, an amide group, an amino group, a cyano group and an alkyl group having the aforementioned group are more preferable. Specific examples of the substituent include —OH, —CH$_2$OH, —CH$_2$CH$_2$OH, —CH$_2$CH$_2$CH$_2$OH; —OCH$_3$, —OCH$_2$CH$_3$, —OCH$_2$CH$_2$CH$_3$; —OCH$_2$OH, —OCH$_2$CH$_2$OH, —OCH$_2$CH$_2$OH; —CONH$_2$, —CH$_2$CONH$_2$, —CH$_2$CH$_2$CONH$_2$; —NH$_2$, —CH$_2$NH$_2$, —CH$_2$CH$_2$NH$_2$, —CH$_2$CH$_2$CH$_2$NH$_2$; —CN, —CH$_2$CN, —CH$_2$CH$_2$CN and the like.

Furthermore, among the substituents, the substituent which is selected from a hydroxyl group, an amino group, an amide group and an alkyl group having the aforementioned functional group are particularly preferable, as they are polar groups which are capable of forming a hydrogen bond. When the alicyclic structure having 3 to 13 carbon atoms has one or more substituents which are selected from them, adsorption of a lubricating layer to a protective layer is improved due to an interaction between the aforementioned substituent and a protective film which is disposed in contact with a lubricating layer containing the fluorine-containing ether compound. As the result, a lubricant containing the fluorine-containing ether compound becomes more excellent in chemical substance resistance, which is preferable.

In the fluorine-containing ether compound represented by the formula (1), a bonding between an organic group represented by $R^1$ and a linking group $R^2$ represented by the formula (2) is preferably a bonding between an atom which is any one of a carbon atom, an oxygen atom and a nitrogen atom included in $R^1$ and a carbon atom included in $R^2$, and is more preferably a bonding between an oxygen atom or a nitrogen atom included in $R^1$ and a carbon atom included in $R^2$ from the viewpoint of easy synthesis. In particular, it is preferable that an organic group represented by $R^1$ and a carbon atom included in $R^2$ are bonded by an ether bond (—O—) by an oxygen atom included in $R^1$. In this case, the molecular structure of the fluorine-containing ether compound represented by the formula (1) is appropriately flexible. Therefore, adhesion between a lubricating layer containing the fluorine-containing ether compound represented by the formula (1) and a protective layer becomes more excellent, which is preferable.

When the alicyclic structure having 3 to 13 carbon atoms included in the organic group represented by $R^1$ is represented by Z, specific examples of a bonding between the alicyclic structure Z and a carbon atom included in $R^2$ include Z—$R^2$, Z—O—$R^2$, Z—NH—$R^2$, Z—CH$_2$O—$R^2$, Z—CH$_2$CH$_2$O—$R^2$, Z—CH$_2$CH$_2$CH$_2$O—$R^2$, Z—CH$_2$—$R^2$, Z—CH$_2$CH$_2$—$R^2$, Z—CH$_2$CH$_2$CH$_2$—$R^2$, Z—CH$_2$CH$_2$CH$_2$CH$_2$—$R^2$ and the like.

In the fluorine-containing ether compound represented by the formula (1), an organic group represented by $R^1$ and a carbon group of a linking group $R^2$ represented by the formula (2) are preferably bonded by an ether bond (—O—) by an oxygen atom which bonds to the alicyclic structure having 3 to 13 carbon atoms included in the organic group represented by $R^1$. (That is, a bonding between the alicyclic structure Z and a carbon atom included in $R^2$ is preferably Z—O—$R^2$.) In this case, a lubricating layer containing the fluorine-containing ether compound represented by the formula (1) has more excellent adhesion to the protective layer, which is preferable.

In the fluorine-containing ether compound of the present embodiment, an organic group represented by $R^1$ bonds to $R^2$ having one to three hydroxyl groups (—OH). Therefore, in a lubricating layer containing the fluorine-containing ether compound of the present embodiment, due to the effect of increasing adhesion to the protective layer which is provided by a hydroxyl group included in $R^2$, the organic group represented by $R^1$ is likely to be arranged close to a protective layer, and a function of improving heat resistance due to the organic group represented by $R^1$ works effectively.

(Linking Group ($R^2$) Represented by Formula (2))

In the fluorine-containing ether compound shown by the formula (1) of the present embodiment, $R^2$ is represented by the formula (2). a in the formula (2) is an integer of 1 to 3. Since a in the formula (2) is 1 or more, a lubricant containing the fluorine-containing ether compound can form a lubricating layer which has excellent adhesion to the protective layer and a high coating rate. In addition, since a in the formula (2) is 3 or less, the number of the hydroxyl group in $R^2$ becomes appropriate, and the polarity of the fluorine-containing ether compound does not become excessively high by having too many hydroxyl groups in $R^2$. Therefore, it is possible to prevent a lubricating layer containing the fluorine-containing ether compound from being attached to a magnetic head as foreign matter (smear) due to the excessively high polarity of the fluorine-containing ether compound and it is possible to suppress pickup. In addition, since $R^2$ is a group represented by the formula (2), in a case where a is 2 or 3, the hydroxyl groups in $R^2$ are disposed at an appropriate distance. a in the formula (2) is preferably 1 to 2, and is still more preferably 1.

(Perfluoropolyether Chain Represented by $R^3$)

In the fluorine-containing ether compound represented by the formula (1), $R^3$ is a perfluoropolyether chain (PFPE chain). The fluorine-containing ether compound represented by the formula (1) preferably includes only one PFPE chain in the molecule. In a case where only one PFPE chain is included in the molecule, no PFPE chain is included in $R^1$ and $R^4$ in the formula (1). When one PFPE chain is included in the molecule, the fluorine-containing ether compound is less likely to be aggregated with each other. Therefore, the lubricating layer including the fluorine-containing ether compound is likely to be disposed in a state of spreading and extending uniformly in the plane direction on the protective layer, which is preferable.

$R^3$ is not particularly limited and can be appropriately selected in accordance with properties required for lubricants containing a fluorine-containing ether compound.

$R^3$ is preferably any of the following formulae (3) to (5). In a case where $R^3$ is any of the formulae (3) to (5), the synthesis of the fluorine-containing ether compound is easy, which is preferable.

In a case where $R^3$ is any of the formulae (3) to (5), the ratio of the number of oxygen atoms (the number of ether bonds (—O—)) to the number of carbon atoms in the perfluoropolyether chain is appropriate. Therefore, the fluorine-containing ether compound becomes a compound with appropriate hardness. Therefore, the fluorine-containing ether compound applied onto a protective layer is less likely to be aggregated on the protective layer, and it is possible to form a lubricating layer having an even thinner thickness at a sufficient coating rate. In addition, in a case where $R^3$ is any of the formulae (3) to (5), the fluorine-containing ether compound becomes a compound from which a lubricating layer having favorable chemical substance resistance can be obtained.

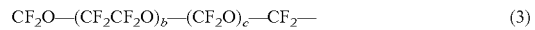
$$CF_2O-(CF_2CF_2O)_b-(CF_2O)_c-CF_2- \quad (3)$$

(b and c in the formula (3) indicate the average degrees of polymerization and each independently represents 0 to 30. Here, there is no case where b and c become 0 at the same time.)

In the formula (3), the arrangement sequence of ($CF_2$—$CF_2$—O) and ($CF_2$—O), which are repeating units, is not particularly limited. In the formula (3), the number b of ($CF_2$—$CF_2$—O)'s and the number c of ($CF_2$—O)'s may be the same or may be different from each other. Here, there is no case where b and c become 0 at the same time. The formula (3) may include any of a random copolymer, a block copolymer, and an alternating copolymer composed of the monomer units ($CF_2$—$CF_2$—O) and ($CF_2$—O).

In a case where $R^3$ in the formula (1) is the formula (3), b that indicates the average degree of polymerization is 0 to 30, preferably 1 to 20, and more preferably 1 to 15. b may be 1 to 10, or 1 to 5. In a case where $R^3$ in the formula (1) is the formula (3), c that indicates the average degree of polymerization is 0 to 30, preferably 0 to 20, and more preferably 0 to 15. c may be 1 to 10, or 1 to 5. When c is 0, b is preferably 1 to 17.

$$CF(CF_3)-(OCF(CF_3)CF_2)_d-OCF(CF_3)- \quad (4)$$

(d in the formula (4) indicates the average degree of polymerization and represents 0.1 to 30.)

In the formula (4), in a case where d that indicates the average degree of polymerization is 0.1 to 30, the number-average molecular weight of the fluorine-containing ether compound of the present embodiment is likely to be within a suitable range. d is preferably 1 to 30, more preferably 2 to 20, and still more preferably 3 to 10.

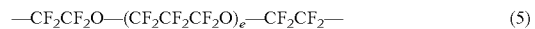
$$-CF_2CF_2O-(CF_2CF_2CF_2O)_e-CF_2CF_2- \quad (5)$$

(e in the formula (5) indicates an average degree of polymerization and represents 0.1 to 30.)

In the formula (5), in a case where e that indicates the average degree of polymerization is 0.1 to 30, the number-average molecular weight of the fluorine-containing ether compound of the present embodiment is likely to be within a suitable range. e is preferably 1 to 20, more preferably 2 to 15, and still more preferably 2 to 8.

(Terminal Group Represented by $R^4$)

In the fluorine-containing ether compound represented by the formula (1), $R^4$ is a terminal group having two or three polar groups, in which individual polar groups bond to different carbon atoms and the carbon atoms to which the polar groups bond are bonded to each other through a linking group having a carbon atom to which the polar groups do not bond. The terminal group represented by $R^4$ preferably includes no perfluoropolyether chains (PFPE chains).

Since the number of the polar groups that are included in $R^4$ is two or three, a lubricant containing the fluorine-containing ether compound has excellent adhesion to a protective layer and is capable of forming a lubricating layer having a high coating rate. The number of the polar groups that are included in $R^4$ is preferably two. When the number of the polar groups that are included in $R^4$ is too large, the polarity of the fluorine-containing ether compound becomes too high, and thus pickup, which is the adhesion of a lubricating layer containing the fluorine-containing ether compound to a magnetic head as foreign matter (smear), is likely to occur. In the present embodiment, since the number of the polar groups that are included in $R^4$ is two or three, it is possible to suppress the occurrence of pickup arising from the excessively high polarity of the fluorine-containing ether compound.

As the two or three polar groups in the terminal group represented by $R^4$, examples include a hydroxyl group (—OH), an amino group (—NH$_2$), a carboxyl group (—COOH), a mercapto group (—SH) and the like. An ether bond (—O—) is not included in the polar groups in $R^4$. Among the aforementioned polar groups, a hydroxyl group is particularly preferable as the polar group. The two or three polar groups that are included in the terminal group represented by $R^4$ may be different from each other or may be all the same, but are all preferably hydroxyl groups.

The hydroxyl group has a strong interaction with a protective layer of a magnetic recording medium, particularly, a protective layer formed of a carbon-based material. Therefore, when some or all of the two or three polar groups in the terminal group represented by $R^4$ are hydroxyl groups, a lubricating layer containing the fluorine-containing ether compound becomes even more excellent in adsorption to protective films, which is preferable.

The terminal group represented by $R^4$ preferably includes an ether bond. In the terminal group represented by $R^4$, it is preferable that two or three polar groups bond to different carbon atoms, and the carbon atoms to which the polar groups bond are bonded to each other through a linking group having an oxygen atom (a linking group having —O— (an ether bond)). The linking group which includes an ether bond imparts flexibility to the molecular structure of the fluorine-containing ether compound which has the terminal group represented by $R^4$. When the carbon atoms to which the polar groups bond are bonded to each other through a linking group having an ether bond, the lubricating layer containing the aforementioned compound is easily adsorbed to the protective film and is excellent in terms of adhesion between the lubricating layer and the protective layer, compared with, for example, a fluorine-containing ether compound in which two hydroxyl groups that are included in a terminal group bond to different carbon atoms, and the carbon atoms to which the hydroxyl groups bond are bonded to each other.

The terminal group represented by $R^4$ in the formula (1) can be appropriately selected depending on performance or the like required for lubricants containing the fluorine-containing ether compound.

$R^4$ in the formula (1) is preferably a terminal group which is any of the following formulae (6) to (9). Such a $R^4$ contributes to impart a high coating rate and excellent adhesion between a protective layer to which a lubricant containing the fluorine-containing ether compound of the present embodiment is applied and a lubricating layer formed by applying the lubricant.

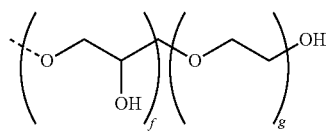

(6)

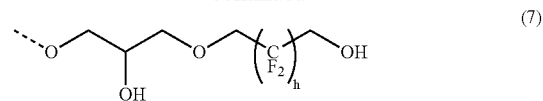

(7)

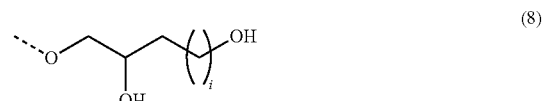

(8)

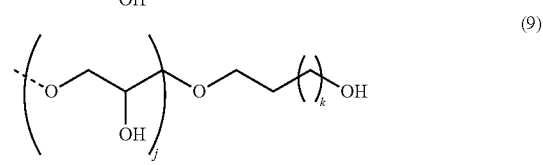

(9)

(In the formula (6), f represents an integer of 1 or 2, and g represents an integer of 1 to 5.)

(In the formula (7), h represents an integer of 2 to 5.)

(In the formula (8), i represents an integer of 1 to 5.)

(In the formula (9), j represents an integer of 1 or 2, and k represents an integer of 1 or 2.)

In the formula (6), f is an integer of 1 or 2, and is preferably 2 from the viewpoint of the adhesion to a protective layer.

In the formula (6), g is an integer of 1 to 5. When g is an integer of 1 to 5, the distance between the hydroxyl groups in the terminal group represented by the formula (6) becomes appropriate, and the fluorine-containing ether compound becomes excellent in terms of adhesion to a protective layer and is capable of forming a lubricating layer having a high coating rate. g is preferably 1 or 2 and most preferably 1 from the viewpoint of the adhesion to a protective layer.

In the formula (7), h is an integer of 2 to 5. In this case, the distance between the hydroxyl group on the $R^3$ side and the hydroxyl group at the terminal becomes appropriate, and the fluorine-containing ether compound becomes excellent in terms of adhesion to a protective layer and is capable of forming a lubricating layer having a high coating rate. h is preferably 2 or 3 and most preferably 2 from the viewpoint of the adhesion to a protective layer.

In the formula (8), i is an integer of 1 to 5. In this case, the distance between the hydroxyl group on the $R^3$ side and the hydroxyl group at the terminal becomes appropriate, and the fluorine-containing ether compound becomes excellent in terms of adhesion to a protective layer and is capable of forming a lubricating layer having a high coating rate. i is preferably 1 or 2 and most preferably 1 from the viewpoint of the adhesion to a protective layer.

In the formula (9), j represents an integer of 1 or 2, and is preferably 2 from the viewpoint of the adhesion to a protective layer.

In the formula (9), k represents an integer of 1 or 2. In this case, the distance between the hydroxyl group on the $R^3$ side and the hydroxyl group at the terminal becomes appropriate, and the fluorine-containing ether compound becomes excellent in terms of adhesion to a protective layer and is capable of forming a lubricating layer having a high coating rate. k is preferably 1 from the viewpoint of the adhesion to a protective layer.

Furthermore, in the fluorine-containing ether compound of the present embodiment, one to three hydroxyl groups which are included in $R^2$ and two or three polar groups which are included in $R^4$ with an appropriate distance are located at both ends of $R^3$ through a methylene group (—CH$_2$—) with good balance. Due to the structure, the lubricating layer containing the fluorine-containing ether compound of the present embodiment has excellent adherence (adhesion) to a protective layer and can coat the surface of the protective layer at a high coating rate. Therefore, the lubricating layer containing the fluorine-containing ether compound of the present embodiment has excellent chemical substance resistance, can be further reduced in thickness and is capable of contributing to reduction in magnetic spacing in magnetic recording media.

The fluorine-containing ether compound represented by the formula (1) is, specifically, preferably any of a compound represented by the following formulae (A) to (O) and (T) to (X).

The numbers of repetition indicated by ba to bm and ca to cm in the formulae (A) to (M), bn in the formula (N), eo in the formula (O) and bt to bx and ct to cx in the formulae (T) to (X) are values indicating the average degrees of polymerization and are not necessarily integers.

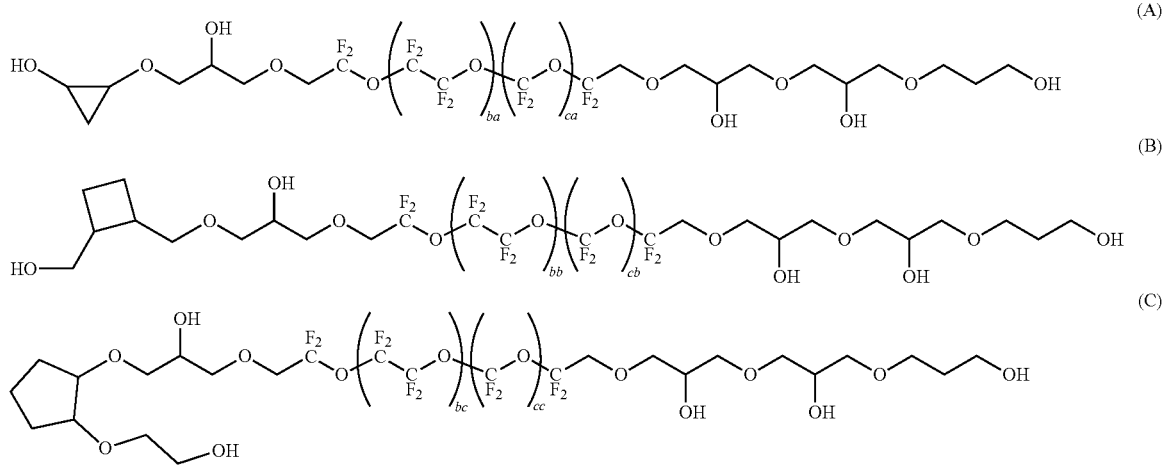

(In the formula (A), ba and ca indicate average degrees of polymerization, ba represents 0 to 30, and ca represents 0 to 30. Here, there is no case where ba and ca become 0 at the same time.)

(In the formula (B), bb and cb indicate average degrees of polymerization, bb represents 0 to 30, and cb represents 0 to 30. Here, there is no case where bb and cb become 0 at the same time.)

(In the formula (C), bc and cc indicate average degrees of polymerization, bc represents 0 to 30, and cc represents 0 to 30. Here, there is no case where bc and cc become 0 at the same time.)

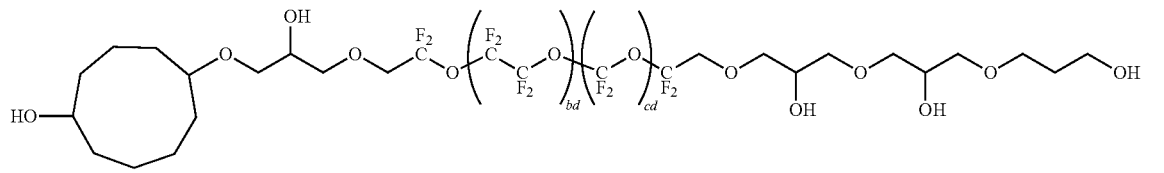

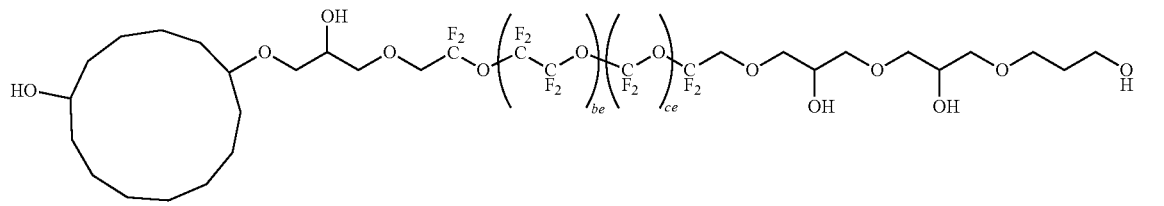

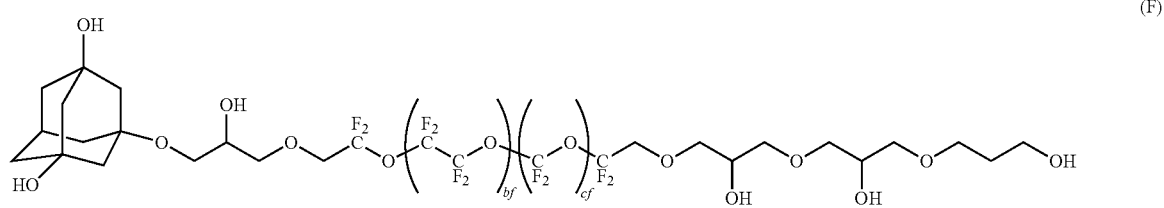

(In the formula (D), bd and cd indicate average degrees of polymerization, bd represents 0 to 30, and cd represents 0 to 30. Here, there is no case where bd and cd become 0 at the same time.)

(In the formula (E), be and ce indicate average degrees of polymerization, be represents 0 to 30, and ce represents 0 to 30. Here, there is no case where be and ce become 0 at the same time.)

(In the formula (F), bf and cf indicate average degrees of polymerization, bf represents 0 to 30, and cf represents 0 to 30. Here, there is no case where bf and cf become 0 at the same time.)

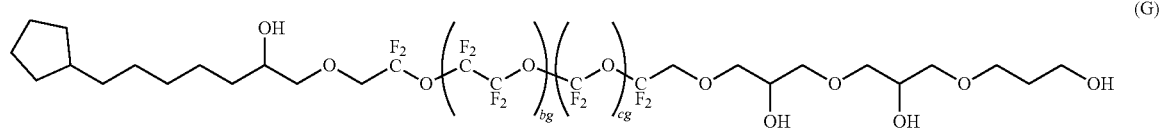

(G)

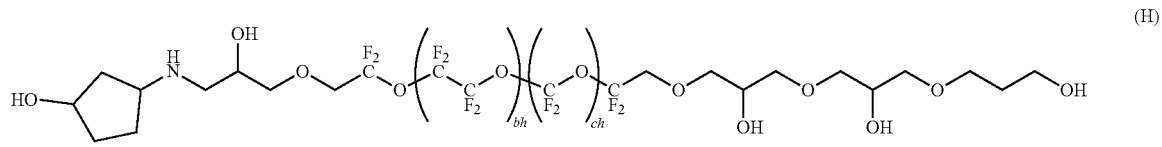

(H)

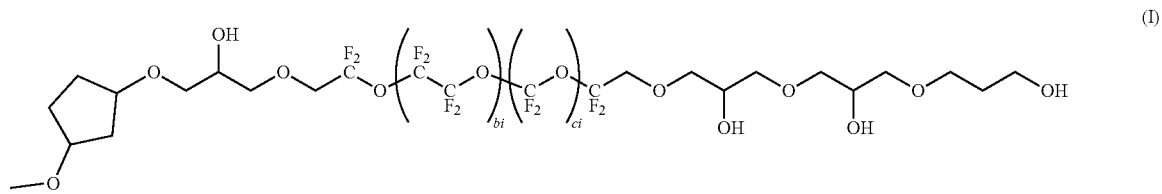

(I)

(In the formula (G), bg and cg indicate average degrees of polymerization, bg represents 0 to 30, and cg represents 0 to 30. Here, there is no case where bg and cg become 0 at the same time.)

(In the formula (H), bh and ch indicate average degrees of polymerization, bh represents 0 to 30, and ch represents 0 to 30. Here, there is no case where bh and ch become 0 at the same time.)

(In the formula (I), bi and ci indicate average degrees of polymerization, bi represents 0 to 30, and ci represents 0 to 30. Here, there is no case where bi and ci become 0 at the same time.)

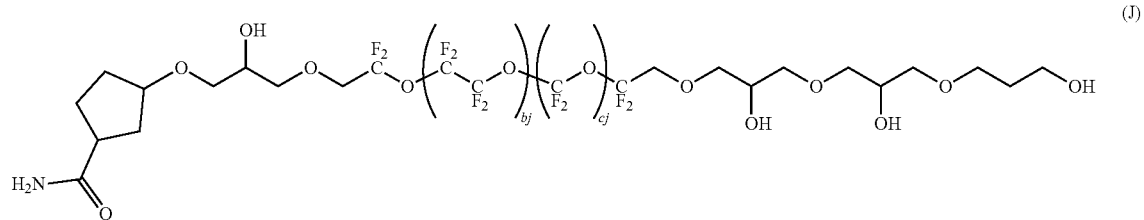

(J)

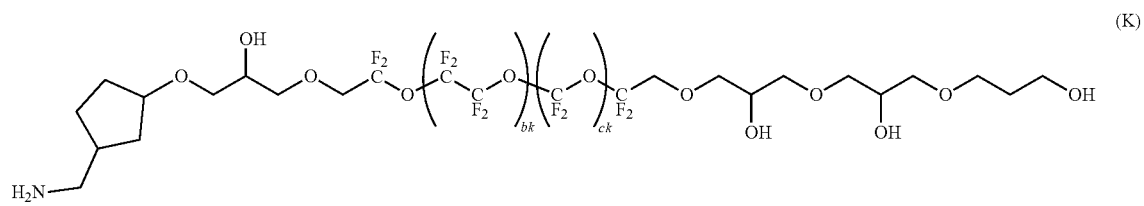

(K)

(In the formula (J), bj and cj indicate average degrees of polymerization, bj represents 0 to 30, and cj represents 0 to 30. Here, there is no case where bj and cj become 0 at the same time.)

(In the formula (K), bk and ck indicate average degrees of polymerization, bk represents 0 to 30, and ck represents 0 to 30. Here, there is no case where bk and ck become 0 at the same time.)

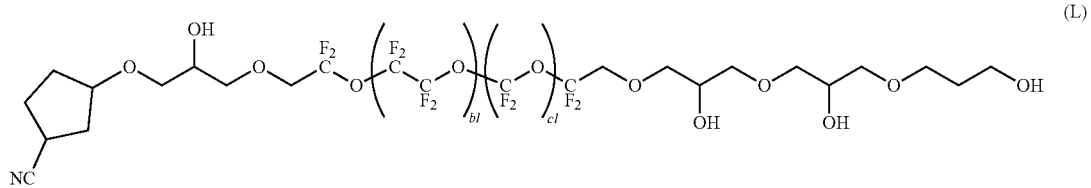

(L)

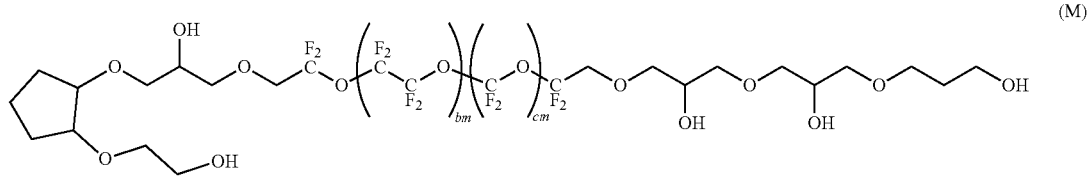

(M)

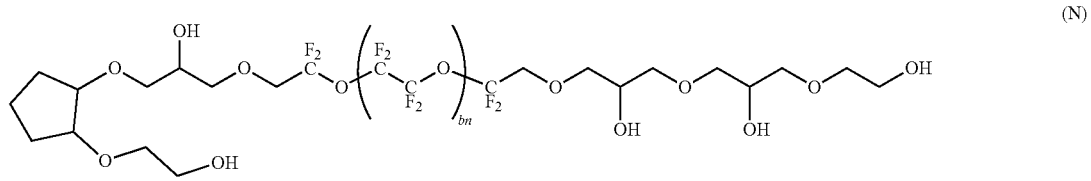

(N)

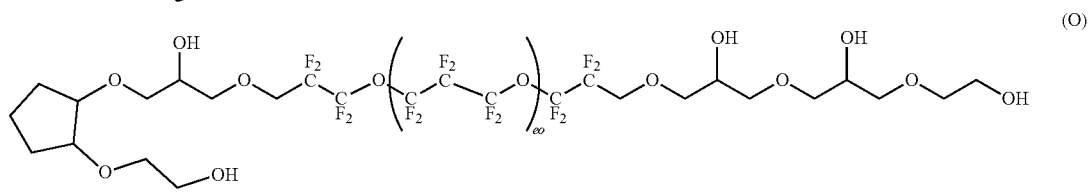

(O)

(In the formula (L), bl and cl indicate average degrees of polymerization, bl represents 0 to 30, and cl represents 0 to 30. Here, there is no case where bl and cl become 0 at the same time.)

(In the formula (M), bm and cm indicate average degrees of polymerization, bm represents 0 to 30, and cm represents 0 to 30. Here, there is no case where bm and cm become 0 at the same time.)

(In the formula (N), bn indicates an average degree of polymerization, and bn represents 0.1 to 30.)

(In the formula (O), eo indicates an average degree of polymerization, and eo represents 0.1 to 30.)

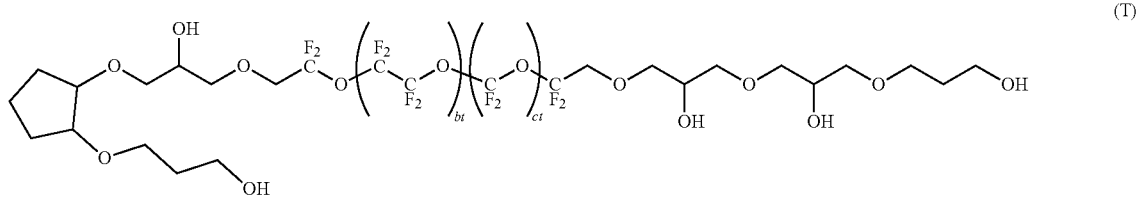

(T)

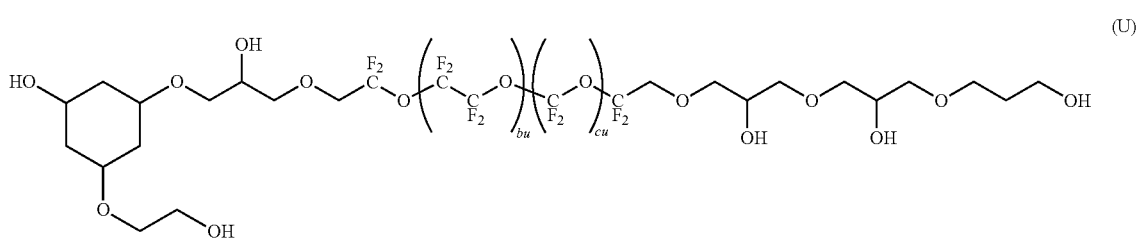

(U)

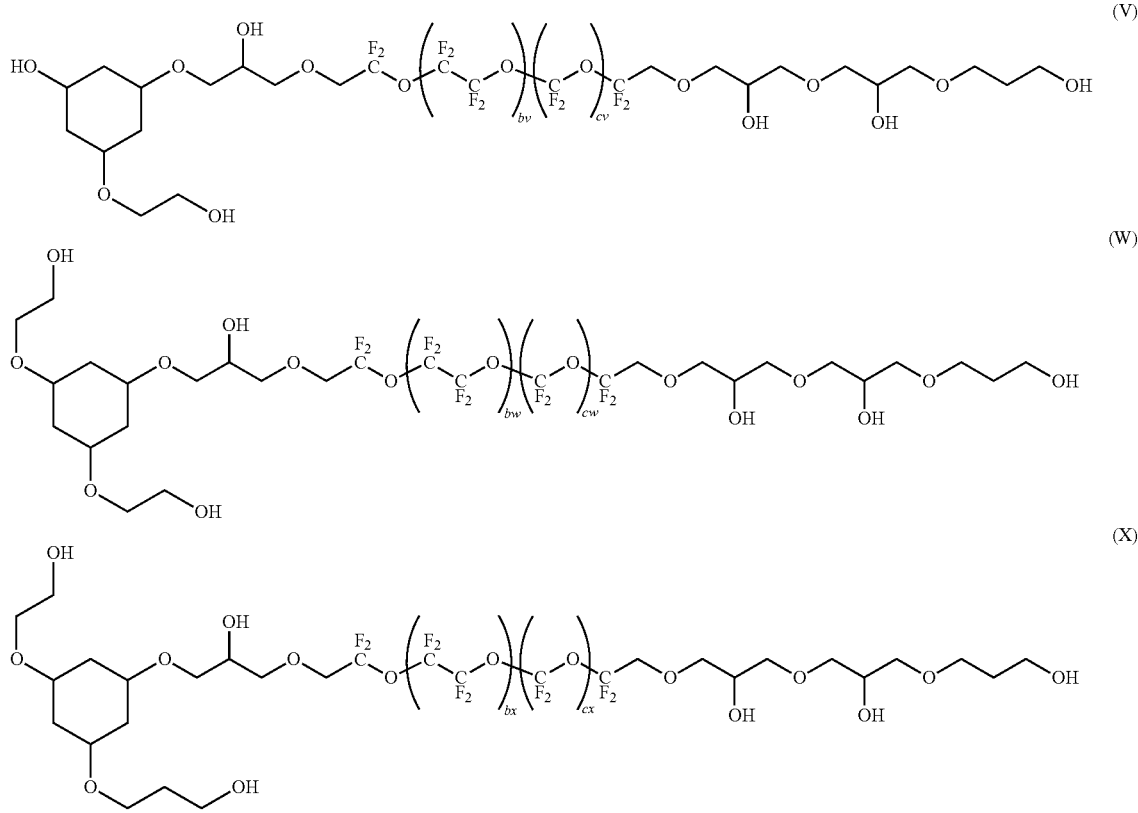

(In the formula (T), bt and ct indicate average degrees of polymerization, bt represents 0 to 30, and ct represents 0 to 30. Here, there is no case where bt and ct become 0 at the same time.)

(In the formula (U), bu and cu indicate average degrees of polymerization, bu represents 0 to 30, and cu represents 0 to 30. Here, there is no case where bu and cu become 0 at the same time.)

(In the formula (V), by and cv indicate average degrees of polymerization, by represents 0 to 30, and cv represents 0 to 30. Here, there is no case where by and cv become 0 at the same time.)

(In the formula (W), bw and cw indicate average degrees of polymerization, bw represents 0 to 30, and cw represents 0 to 30. Here, there is no case where bw and cw become 0 at the same time.)

(In the formula (X), bx and cx indicate average degrees of polymerization, bx represents 0 to 30, and cx represents 0 to 30. Here, there is no case where bx and cx become 0 at the same time.)

In the compounds represented by the formulae (A) to (O) and (T) to (X), all of $R^2$'s are represented by formula (2), and a in $R^2$ is 1. In the compounds represented by the formulae (A) to (N) and (T) to (X), $R^3$'s are represented by formula (3), and in the compound represented by the formula (O), $R^3$ is represented by formula (5).

In the compounds represented by the formulae (A) to (L) and (T) to (X), all of $R^4$'s are represented by formula (9), and in the formula (9), j is 2 and k is 1. In the compounds represented by the formulae (M) to (0), $R^4$'s are represented by formula (6), and in the formula (6), f is 2 and g is 1.

In the compound represented by the formula (A), an alicyclic structure of $R^1$ is cyclopropane.

In the compound represented by the formula (B), an alicyclic structure of $R^1$ is cyclobutane.

In the compound represented by the formula (C), an alicyclic structure of $R^1$ is cyclopentane.

In the compound represented by the formula (D), an alicyclic structure of $R^1$ is cyclononane.

In the compound represented by the formula (E), an alicyclic structure of $R^1$ is cyclotridecane.

In the compound represented by the formula (F), an alicyclic structure of $R^1$ is adamantane.

In the compounds represented by the formulae (G) to (O), and (T), an alicyclic structure of $R^1$ is cyclopentane.

In the compounds represented by the formulae (U) to (X), an alicyclic structure of $R^1$ is cyclohexane.

In the formulae, ba to bm and bt to bx may be 0, may be 1 to 20, may be 1 to 10, or may be 1 to 5. ca to cm, and ct to cx may be 0, may be 1 to 20, may be 1 to 10, or 1 to 5. bn and eo may be 1 to 20, may be 1 to 10, or may be 1 to 5.

When the compound represented by the formula (1) is any one of the compounds represented by the formulae (A) to (O), and (T) to (X), a raw material is easy to obtain, and it is possible to form a lubricating layer which has more excellent heat resistance and chemical substance resistance and can furthermore suppress pickup in spite of a thin thickness, which is preferable.

The number-average molecular weight (Mn) of the fluorine-containing ether compound of the present embodiment is preferably within a range of 500 to 10000, more preferably within a range of 700 to 7000, and particularly preferably within a range of 1000 to 3000. When the number-average molecular weight is 500 or more, lubricants containing the fluorine-containing ether compound of the present embodiment are less likely to evaporate, and it is possible to prevent the lubricants from evaporating and transferring to a magnetic head. In addition, when the number-average molecular weight is 10000 or less, the viscosity of the fluorine-containing ether compound becomes appropriate, and application of lubricants containing this fluorine-containing ether compound makes it possible to easily form a lubricating layer having a thin thickness. When the number-average molecular weight is 3000 or less, in a case where the fluorine-containing ether compound is applied to lubricants, the lubricants have appropriate viscosity for handling, which is preferable.

The number-average molecular weight (Mn) of the fluorine-containing ether compound is a value measured by $^1$H-NMR and $^{19}$F-NMR with AVANCE 111400 manufactured by Bruker BioSpin Group. In the nuclear magnetic resonance (NMR) measurement, a sample is diluted with a single or mixed solvent of hexafluorobenzene, acetone-d, tetrahydrofuran-d and the like and used in the measurement. As the reference of the $^{19}$F-NMR chemical shift, the peak of hexafluorobenzene was set to −164.7 ppm, and, as the reference of the $^1$H-NMR chemical shift, the peak of acetone was set to 2.2 ppm.

"Production Method"

A method for producing the fluorine-containing ether compound of the present embodiment is not particularly limited, and the fluorine-containing ether compound can be produced using a well-known conventional production method. The fluorine-containing ether compound of the present embodiment can be produced using, for example, a production method to be described below.

First, HO—CH$_2$—R$^3$—CH$_2$—OH which is a compound corresponding to —CH$_2$—R$^3$—CH$_2$— in the formula (1) is synthesized. Next, an addition reaction is carried out to the compound with an epoxide which provides an alicyclic structure corresponding to R$^1$—R$^2$— in the formula (1). As the result, a compound represented by the following formula (1-1) is generated.

R$^1$—R$^2$—CH$_2$—R$^3$—CH$_2$—OH    (1-1)

(In the formula (1-1), R$^1$, R$^2$ and R$^3$ are respectively the same as R$^1$, R$^2$ and R$^3$ in the formula (1)).

The epoxide which provides an alicyclic structure corresponding to R$^1$—R$^2$— in the formula (1) and is used as a raw material of a compound represented by the formula (1-1) can be generated by, for example, an addition reaction of an alcohol having an alicyclic structure corresponding to R$^1$ in the formula (1) with epibromohydrin.

Specifically, for example, when an alicyclic structure corresponding to R$^1$ in the formula (1) is cyclopentane, an epoxide which provides an alicyclic structure corresponding to R$^1$—R$^2$— in the formula (1) can be generated by an addition reaction of cyclopentanol and epibromohydrin.

Next, the compound represented by the general formula (1-1) and an epoxide having one or more polar groups are reacted with each other to generate a fluorine-containing ether compound represented by the formula (1), in which a hydroxyl group (—OH) located at an end of the compound represented by formula (1-1) is substituted by R$^4$ of the formula (1).

The epoxide having one or more polar groups can be generated, for example, by an addition reaction of ethylene glycol with epibromohydrin.

The generated fluorine-containing ether compound represented by the formula (1) is preferably purified, for example, by a method in which column chromatography is used.

The compound represented by the formula (1) is obtained by the aforementioned method.

The fluorine-containing ether compound of the present embodiment is a compound represented by the aforementioned formula (1). Accordingly, when a lubricating layer is formed by applying a lubricant containing the fluorine-containing ether compound onto a protective layer, the PFPE chain represented by R$^3$ in the formula (1) coats the surface of the protective layer and reduces a friction force between a magnetic head and the protective layer. In addition, the lubricating layer which is formed by applying the lubricant containing the fluorine-containing ether compound of the present embodiment has excellent heat resistance, as an alicyclic structure included in the organic group represented by R$^1$ has heat stability.

In addition, the lubricating layer which includes the fluorine-containing ether compound of the present embodiment is adhered onto the protective layer by the bond between one to three hydroxyl groups included in the linking group represented by R$^2$ in the fluorine-containing ether compound and the protective layer and the bond between two or three polar groups included in the terminal group represented by R$^4$ and the protective layer.

Furthermore, in the fluorine-containing ether compound of the present embodiment, two or three polar groups included in the terminal group represented by R$^4$ bond to different carbon atoms and the carbon atoms to which the polar groups bond are bonded to each other through a linking group. Accordingly, the lubricating layer which includes the fluorine-containing ether compound of the present embodiment has favorable flexibility. Therefore, the lubricating layer containing the fluorine-containing ether compound of the present embodiment is easily adsorbed to the protective film and has excellent adhesion to the protective layer.

As described above, according to the fluorine-containing ether compound of the present embodiment, the lubricating layer and the protective layer are strongly bonded to each other, and a lubricating layer which has excellent heat resistance and chemical substance resistance and can suppress pickup can be obtained.

[Lubricant for Magnetic Recording Medium]

A lubricant for a magnetic recording medium of the present embodiment contains the fluorine-containing ether compound represented by the formula (1).

The lubricant of the present embodiment can be used after being mixed as necessary with a well-known material that is used as a material for lubricants as long as characteristics attributed to the fluorine-containing ether compound represented by the formula (1) contained in the lubricant are not impaired.

Specific examples of well-known materials include FOMBLIN (registered trademark) ZDIAC, FOMBLIN ZDEAL, FOMBLIN AM-2001 (all manufactured by Solvay Solexis), Moresco A20H (manufactured by Moresco Corporation) and the like. The number-average molecular weight of the well-known material that is used by being mixed with the lubricant of the present embodiment is preferably 1000 to 10000.

In a case where the lubricant of the present embodiment contains a material other than the fluorine-containing ether compound represented by the formula (1), the content of the fluorine-containing ether compound represented by the formula (1) in the lubricant of the present embodiment is preferably 50 mass % or more and more preferably 70 mass % or more. The content of the fluorine-containing ether compound represented by formula (1) may be 80 mass % or more, or 90 mass % or more. The upper limit can be arbitrarily selected and may be, for example, 99 mass % or less, 95 mass % or less, or 90 mass % or less.

The lubricant of the present embodiment contains the fluorine-containing ether compound represented by the formula (1) and is thus capable of coating the surface of a protective layer at a high coating rate in spite of a thin thickness and is capable of forming a lubricating layer having excellent adhesion to the protective layer. Therefore, according to the lubricant of the present embodiment, a lubricating layer, which has excellent chemical substance resistance and heat resistance and can suppress pickup, can be obtained in spite of a thin thickness.

[Magnetic Recording Medium]

A magnetic recording medium of the present embodiment includes at least a magnetic layer, a protective layer and a lubricating layer sequentially provided on a substrate.

In the magnetic recording medium of the present embodiment, one or more underlayers can be provided as necessary between the substrate and the magnetic layer. In addition, it is also possible to provide an adhesive layer and/or a soft magnetic layer between the underlayer and the substrate.

FIG. 1 is a schematic cross-sectional view showing an embodiment of the magnetic recording medium of the present invention.

A magnetic recording medium 10 of the present embodiment has a structure in which an adhesive layer 12, a soft magnetic layer 13, a first underlayer 14, a second underlayer 15, a magnetic layer 16, a protective layer 17 and a lubricating layer 18 are sequentially provided on a substrate 11.

"Substrate"

As the substrate 11, for example, a non-magnetic substrate or the like wherein a film formed of NiP or NiP alloy is formed on a base which is made of a metal or alloy material such as Al or an Al alloy can be used.

In addition, as the substrate 11, a non-magnetic substrate made of a non-metal material such as glass, ceramic, silicon, silicon carbide, carbon or resin may be used, and a non-magnetic substrate wherein a film formed of NiP or NiP alloy is formed on a base made of the aforementioned non-metal material may also be used.

"Adhesive Layer"

The adhesive layer 12 prevents the progress of corrosion of the substrate 11 which may occur in a case where the substrate 11 and the soft magnetic layer 13, which is provided on the adhesive layer 12, are disposed in contact with each other.

The material of the adhesive layer 12 can be appropriately selected from, for example, Cr, a Cr alloy, Ti, a Ti alloy, CrTi, NiAl, an AlRu alloy and the like. The adhesive layer 12 can be formed by, for example, a sputtering method.

"Soft Magnetic Layer"

The soft magnetic layer 13 preferably has a structure in which a first soft magnetic film, an interlayer made of a Ru film and a second soft magnetic film are sequentially laminated. That is, the soft magnetic layer 13 preferably has a structure in which the interlayer made of a Ru film is sandwiched between the two soft magnetic films and thereby the soft magnetic films on and under the interlayer are antiferromagnetically coupled (AFC).

As the material of the first soft magnetic film and the second soft magnetic film, examples include a CoZrTa alloy, a CoFe alloy and the like.

To the CoFe alloy that is used for the first soft magnetic film and the second soft magnetic film, any of Zr, Ta and Nb is preferably added. This accelerates the amorphization of the first soft magnetic film and the second soft magnetic film, makes it possible to improve the orientation of the first underlayer (seed layer) and makes it possible to reduce the flying height of a magnetic head.

The soft magnetic layer 13 can be formed by, for example, a sputtering method.

"First Underlayer"

The first underlayer 14 is a layer for controlling the orientations and/or crystal sizes of the second underlayer 15 and the magnetic layer 16 that are provided on the first underlayer 14.

As the first underlayer 14, examples include a Cr layer, a Ta layer, a Ru layer, a CrMo alloy layer, a CoW alloy layer, a CrW alloy layer, a CrV alloy layer, a CrTi alloy layer, and the like.

The first underlayer 14 can be formed by, for example, a sputtering method.

"Second Underlayer"

The second underlayer 15 is a layer that controls the orientation of the magnetic layer 16 to be favorable. The second underlayer 15 is preferably a layer formed of Ru or a Ru alloy.

The second underlayer 15 may be a single layer or may be composed of a plurality of layers. In a case where the second underlayer 15 is composed of a plurality of layers, all of the layers may be composed of the same material or at least one layer may be composed of a different material.

The second underlayer 15 can be formed by, for example, a sputtering method.

"Magnetic Layer"

The magnetic layer 16 is made of a magnetic film in which the easy magnetization axis is directed in a perpendicular or parallel direction with respect to the substrate surface. The magnetic layer 16 is, for example, a layer containing Co and Pt and may be a layer further containing an oxide and/or Cr, B, Cu, Ta, Zr or the like in order to improve SNR characteristics.

Examples of the oxide that is contained in the magnetic layer 16 include $SiO_2$, SiO, $Cr_2O_3$, CoO, $Ta_2O_3$, $TiO_2$ and the like.

The magnetic layer 16 may be composed of a single layer or may be composed of a plurality of magnetic layers made of materials with different compositions.

For example, in a case where the magnetic layer 16 is composed of three layers of a first magnetic layer, a second magnetic layer and a third magnetic layer sequentially laminated from below, the first magnetic layer is preferably a granular structure made of a material containing Co, Cr and Pt and further containing an oxide. As the oxide that is contained in the first magnetic layer, for example, oxides of Cr, Si, Ta, Al, Ti, Mg, Co or the like are preferably used. Among them, in particular, $TiO_2$, $Cr_2O_3$, $SiO_2$ and the like can be preferably used. In addition, the first magnetic layer is preferably made of a composite oxide to which two or more oxides have been added. Among them, in particular, $Cr_2O_3$—$SiO_2$, $Cr_2O_3$—$TiO_2$, $SiO_2$—$TiO_2$ and the like can be preferably used.

The first magnetic layer may preferably contain, in addition to Co, Cr, Pt and the oxide, one or more elements selected from B, Ta, Mo, Cu, Nd, W, Nb, Sm, Tb, Ru and Re. For the second magnetic layer, the same material as for the first magnetic layer can be used. The second magnetic layer is preferably a granular structure.

The third layer is preferably a non-granular structure made of a material containing Co, Cr and Pt but containing no oxides. The third magnetic layer may preferably contain, in addition to Co, Cr, and Pt, one or more elements selected from B, Ta, Mo, Cu, Nd, W, Nb, Sm, Tb, Ru, Re and Mn.

In a case where the magnetic layer 16 is formed of a plurality of magnetic layers, a non-magnetic layer is preferably provided between the magnetic layers adjacent to each other. In a case where the magnetic layer 16 is made of three layers of the first magnetic layer, the second magnetic layer and the third magnetic layer, it is preferable to provide a non-magnetic layer between the first magnetic layer and the second magnetic layer and a non-magnetic layer between the second magnetic layer and the third magnetic layer.

For the non-magnetic layer that is provided between the magnetic layers adjacent to each other in the magnetic layer 16, for example, Ru, a Ru alloy, a CoCr alloy, a CoCrX1 alloy (X1 represents one or more elements selected from Pt, Ta, Zr, Re, Ru, Cu, Nb, Ni, Mn, Ge, Si, O, N, W, Mo, Ti, V and B) and the like are preferably used.

For the non-magnetic layer that is provided between the magnetic layers adjacent to each other in the magnetic layer 16, an alloy material containing an oxide, a metallic nitride or a metallic carbide is preferably used. Specifically, as the oxide, for example, $SiO_2$, $Al_2O_3$, $Ta_2O_5$, $Cr_2O_3$, MgO, $Y_2O_3$, $TiO_2$ and the like can be used. As the metallic nitride, for example, AlN, $Si_3N_4$, TaN, CrN and the like can be used. As the metallic carbide, for example, TaC, BC, SiC and the like can be used.

The non-magnetic layer can be formed by, for example, a sputtering method.

The magnetic layer 16 is preferably a magnetic layer for perpendicular magnetic recording in which the easy magnetization axis is directed in a direction perpendicular to the substrate surface in order to realize a higher recording density. The magnetic layer 16 may be a magnetic layer for longitudinal magnetic recording.

The magnetic layer 16 may be formed by any well-known conventional method such as a deposition method, an ion beam sputtering method or a magnetron sputtering method. The magnetic layer 16 is normally formed by a sputtering method.

"Protective Layer"

The protective layer 17 protects the magnetic layer 16. The protective layer 17 may be composed of a single layer or may be composed of a plurality of layers. As the material of the protective layer 17, carbon, nitrogen-containing carbon, silicon carbide and the like can be exemplified.

As the protective layer 17, a carbon-based protective layer can be preferably used, and in particular, an amorphous carbon protective layer is preferable. When the protective layer 17 is a carbon-based protective layer, the interaction with the hydroxyl group that is included in the fluorine-containing ether compound in the lubricating layer 18 is further enhanced, which is preferable.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer is preferably 3 to 20 atomic % when measured by the hydrogen forward scattering method (HFS). In addition, the nitrogen content in the carbon-based protective layer is preferably 4 to 15 atomic % when measured by X-ray photoelectron spectroscopy (XPS).

The hydrogen and/or nitrogen that are contained in the carbon-based protective layer do not need to be uniformly contained throughout the entire carbon-based protective layer. The carbon-based protective layer is preferably formed, for example, as a composition gradient layer in which nitrogen is contained in the lubricating layer 18 side of the protective layer 17 and hydrogen is contained in the magnetic layer 16 side of the protective layer 17. In this case, the adhesive force between the magnetic layer 16 and the carbon-based protective layer and the adhesive force between the lubricating layer 18 and the carbon-based protective layer further improve.

The film thickness of the protective layer 17 can be arbitrarily selected, but is preferably set to 1 nm to 7 nm. When the film thickness of the protective layer 17 is 1 nm or more, performance as the protective layer 17 can be sufficiently obtained. The film thickness of the protective layer 17 is preferably 7 nm or less from the viewpoint of reducing the thickness of the protective layer 17.

As a method for forming the protective layer 17, it is possible to use a sputtering method in which a carbon-containing target is used, a chemical vapor deposition (CVD) method in which a hydrocarbon raw material such as ethylene or toluene is used, an ion beam deposition (IBD) method and the like.

In the case of forming a carbon-based protective layer as the protective layer 17, the carbon-based protective layer can be formed by, for example, a DC magnetron sputtering method. Particularly, in the case of forming a carbon-based protective layer as the protective layer 17, an amorphous carbon protective layer is preferably formed by a plasma CVD method. The amorphous carbon protective layer formed by the plasma CVD method has a uniform surface with small roughness.

"Lubricating Layer"

The lubricating layer 18 prevents contamination of the magnetic recording medium 10. In addition, the lubricating layer 18 reduces a frictional force of a magnetic head of a magnetic recording/reproducing device, which slides on the magnetic recording medium 10, and thereby improves the durability of the magnetic recording medium 10.

The lubricating layer 18 is formed in contact with the protective layer 17 as shown in FIG. 1. The lubricating layer 18 contains the aforementioned fluorine-containing ether compound.

In a case where the protective layer 17, which is disposed below the lubricating layer 18, is a carbon-based protective layer, the lubricating layer 18 is bonded to the protective layer 17 with a particularly high bonding force. As the result, it becomes easy to obtain the magnetic recording medium 10 in which the surface of the protective layer 17 is coated at a high coating rate in spite of a thin thickness of the lubricating layer 18, and it is possible to effectively prevent contamination on the surface of the magnetic recording medium 10.

The average film thickness of the lubricating layer 18 can be arbitrarily selected, but is preferably 0.5 nm (5 Å) to 2 nm (20 Å) and more preferably 0.5 nm (5 Å) to 1 nm (10 Å). When the average film thickness of the lubricating layer 18 is 0.5 nm or more, the lubricating layer 18 does not become an island shape or a mesh shape and is formed in a uniform film thickness. Therefore, the surface of the protective layer 17 can be coated with the lubricating layer 18 at a high coating rate. In addition, when the average film thickness of the lubricating layer 18 is set to 2 nm or less, it is possible to sufficiently reduce the thickness of the lubricating layer 18 and to sufficiently decrease the flying height of a magnetic head.

In a case where the surface of the protective layer 17 is not sufficiently coated with the lubricating layer 18 at a high coating rate, an environmental substance adsorbed to the surface of the magnetic recording medium 10 passes through voids in the lubricating layer 18 and intrudes below the lubricating layer 18. The environmental substance that has intruded below the lubricating layer 18 is adsorbed and bonded to the protective layer 17 and generates a contamination substance. In addition, at the time of reproducing magnetic records, this contamination substance (aggregated component) adheres (transfers) to a magnetic head as a smear to break the magnetic head or degrade the magnetic recording/reproducing characteristics of magnetic recording/reproducing devices.

As the environmental substance that generates the contamination substance, examples include siloxane compounds (cyclic siloxane and linear siloxane), ionic impurities, hydrocarbons having a relatively high molecular weight such as octacosane, plasticizers such as dioctyl phthalate and the like. As a metal ion that is contained in the ionic impurities, examples include a sodium ion, a potassium ion and the like. As an inorganic ion that is contained in the ionic impurities, examples include a chlorine ion, a bromine ion, a nitrate ion, a sulfate ion, an ammonium ion and the like. As an organic ion that is contained in the ionic impurities, examples include an oxalate ion, a formate ion and the like.

"Method for Forming Lubricating Layer"

A method for forming the lubricating layer 18 can be arbitrarily selected and is, for example, a method in which a magnetic recording medium that is not yet fully manufactured and thus includes the individual layers up to the protective layer 17 formed on the substrate 11 is prepared and a solution for forming the lubricating layer is applied and dried on the protective layer 17.

The solution for forming the lubricating layer can be obtained by, for example, dispersing and dissolving the aforementioned lubricant for a magnetic recording medium of the embodiment in a solvent as necessary and adjusting the viscosity and concentration to be suitable for application methods.

Examples of the solvent that is used for the solution for forming the lubricating layer include fluorine-based solvents such as VERTREL (registered trademark) XF (trade name, manufactured by Dupont-Mitsui Fluorochemicals Co., Ltd.) and the like.

The method for applying the solution for forming the lubricating layer is not particularly limited, and examples thereof include a spin coating method, a spraying method, a paper coating method, a dipping method and the like.

In the case of using the dipping method, it is possible to use, for example, a method to be described below. First, the substrate 11 on which the individual layers up to the protective layer 17 have been formed is immersed into the solution for forming the lubricating layer that has been put into an immersion vessel of a dip coater. Next, the substrate 11 is lifted from the immersion vessel at a predetermined speed. This applies the solution for forming the lubricating layer to the surface of the protective layer 17 on the substrate 11.

The use of the dipping method makes it possible to uniformly apply the solution for forming the lubricating layer to the surface of the protective layer 17 and makes it possible to form the lubricating layer 18 on the protective layer 17 in a uniform film thickness.

In the present embodiment, a thermal treatment is preferably carried out on the substrate 11 on which the lubricating layer 18 has been formed. The thermal treatment improves the adhesion between the lubricating layer 18 and the protective layer 17 and improves the adhesive force between the lubricating layer 18 and the protective layer 17.

The thermal treatment temperature can be arbitrarily selected, but is preferably set to 100° C. to 180° C. When the thermal treatment temperature is 100° C. or higher, an effect on improvement in the adhesion between the lubricating layer 18 and the protective layer 17 can be sufficiently obtained. In addition, when the thermal treatment temperature is set to 180° C. or lower, it is possible to prevent thermal decomposition of the lubricating layer 18. The thermal treatment time is preferably set to 10 to 120 minutes.

In the present embodiment, a treatment of irradiating the lubricating layer 18 on the substrate 11 with ultraviolet rays (UV) may be carried out before the thermal treatment or after the thermal treatment, in order to further improve the adhesive force of the lubricating layer 18 to the protective layer 17.

The magnetic recording medium 10 of the present embodiment has at least the magnetic layer 16, the protective layer 17 and the lubricating layer 18 sequentially provided on the substrate 11. In the magnetic recording medium 10 of the present embodiment, the lubricating layer 18 containing the aforementioned fluorine-containing ether compound is formed in contact with the protective layer 17. This lubricating layer 18 coats the surface of the protective layer 17 at a high coating rate in spite of a thin thickness. Therefore, in the magnetic recording medium 10 of the present embodiment, intrusion of the environmental substance that generates the contamination substance such as the ionic impurities through voids in the lubricating layer 18 is prevented. Therefore, the amount of the contamination substance present on the surface of the magnetic recording medium 10 of the present embodiment is small. In addition, in the lubricating layer 18 in the magnetic recording medium 10 of the present embodiment, foreign matter (smear) is less likely to be generated, and pickup can be suppressed. In addition, the lubricating layer 18 in the magnetic recording medium 10 of the present embodiment has excellent chemical substance resistance and heat resistance. Therefore, the magnetic recording medium 10 of the present embodiment has excellent reliability and durability.

EXAMPLES

Hereinafter, the present invention will be more specifically described using examples and comparative examples. The present invention is not limited only to the following examples.

Example 1

A compound represented by the aforementioned formula (A) (in the formula (A), ba which indicates the average degree of polymerization is 4.5, and ca which indicates the average degree of polymerization is 4.5) was obtained by a method to be described below.

First, 1,2-cyclopropanediol and epibromohydrin were reacted to synthesize a compound represented by the following formula (10). In addition, a reaction product which was obtained by reacting 3-allyloxy-1,2-propanediol-2-methoxymethyl ether and 2-(bromopropoxy)tetrahydro-2H-pyran was oxidized to synthesize a compound represented by the following formula (11).

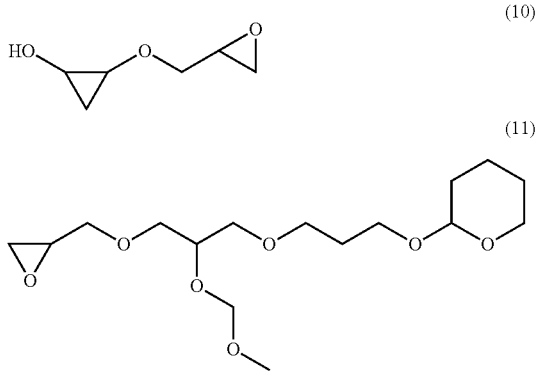

(10)

(11)

A fluoropolyether (number-average molecular weight: 1000, molecular weight distribution: 1.1) (40.0 g) represented by $HOCH_2CF_2O(CF_2CF_2O)_s(CF_2O)_tCF_2CH_2OH$ (in the formula, s which indicates the average degree of polymerization is 4.5 and t which indicates the average degree of polymerization is 4.5), the compound represented by the above formula (10) (6.10 g) and t-BuOH (tertiary butyl alcohol) (40.0 mL) were charged into a 200 mL eggplant flask in a nitrogen gas atmosphere and stirred at room temperature until the components became homogeneous. Furthermore, t-BuOK (potassium tertiary butoxide) (1.35 g) was added to the flask and heated and stirred at 70° C. for 18 hours to be reacted.

Then, the obtained reaction product was cooled to 25° C., water was added thereto, and furthermore VERTREL (registered trademark) XF (hereinafter, it may be described as "VERTREL XF"), which was manufactured by Dupont-Mitsui Fluorochemicals Co., Ltd., was added thereto as a solvent and an organic layer was extracted and washed with water. The organic layer was dehydrated by adding anhydrous sodium sulfate, and after the drying agent was filtered, the filtrate was concentrated. The residue was purified by silica gel column chromatography, thereby obtaining a compound represented by the following formula (12) (17.5 g).

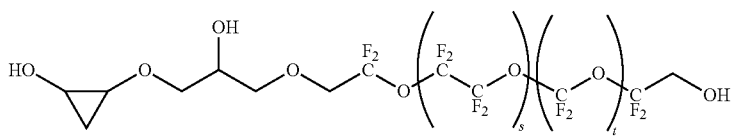

(12)

(In the formula (12), s which indicates the average degree of polymerization is 4.5, and t which indicates the average degree of polymerization is 4.5.)

The compound represented by the above formula (12) (17.5 g), the compound represented by the above formula (11) (2.67 g) and t-BuOH (tertiary butyl alcohol) (65.0 mL) were charged into a 200 mL eggplant flask in a nitrogen gas atmosphere and stirred at room temperature until the components became homogeneous. Furthermore, t-BuOK (potassium tertiary butoxide) (0.235 g) was added to the flask and heated and stirred at 70° C. for 16 hours to be reacted.

Then, the obtained reaction product was cooled to 25° C., water (3.3 mL) and a 5 to 10% hydrogen chloride/methanol (product name: X0041, hydrogen chloride-methanol reagent (5% to 10%), manufactured by Tokyo Chemical Industry Co., Ltd.) (21.5 mL) were added and stirred at room temperature for 3 hours. To the obtained residue, 5% sodium bicarbonate water (100 mL) was added, and it was extracted with ethyl acetate, and the organic layer thereof was washed with water. Then, the organic layer was dehydrated with anhydrous magnesium sulfate, and after the drying agent was filtered, the filtrate was concentrated. The residue was purified by silica gel column chromatography, thereby obtaining 11.1 g of a compound represented by the formula (A).

$^1$H-NMR measurement and $^{19}$F-NMR measurement of the obtained compound (A) were carried out, and the structure was identified from the following results.

$^1$H-NMR (acetone-d$_6$); δ [ppm]=1.2 to 2.0 (4H), 3.20 to 4.20 (30H)

$^{19}$F-NMR (acetone-d$_6$): δ [ppm]=−51.99 to −55.72 (9F), −78.48 (2F), −80.66 (2F), −89.16 to −91.14 (18F)

Example 2

A compound represented by the aforementioned formula (B) (in the formula (B), bb which indicates the average degree of polymerization is 4.5, and cb which indicates the average degree of polymerization is 4.5) was obtained by a method to be described below.

First, 1,2-cyclobutanedimethanol and epibromohydrin were reacted to synthesize a compound represented by the following formula (13).

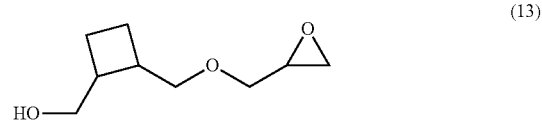 [SMILES: OCC1CCC1COCC1CO1]

(13)

The same operation as in Example 1 was carried out except that 6.10 g of a compound represented by the formula (13) was used instead of the compound represented by formula (10) used in Example 1, thereby obtaining 10.5 g of the compound represented by the formula (B).

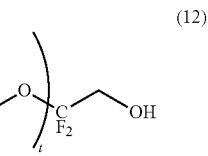

$^1$H-NMR measurement of the obtained compound (B) was carried out, and the structure was identified from the following results.

$^1$H-NMR (acetone-d$_6$); δ [ppm]=1.2 to 2.0 (6H), 3.20 to 4.20 (34H)

Example 3

A compound represented by the aforementioned formula (C) (in the formula (C), be which indicates the average degree of polymerization is 4.5, and cc which indicates the average degree of polymerization is 4.5) was obtained by a method to be described below.

First, 1,2-cyclopentanediol, epibromohydrin and 2-(bromoethoxy)tetrahydro-2H-pyran were reacted to synthesize a compound represented by the following formula (14).

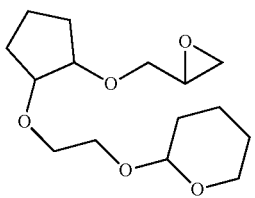

(14)

The same operation as in Example 1 was carried out except that 6.10 g of a compound represented by the formula (14) was used instead of the compound represented by formula (10) used in Example 1, thereby obtaining 11.9 g of the compound represented by the formula (C).

$^1$H-NMR measurement of the obtained compound (C) was carried out, and the structure was identified from the following results.

$^1$H-NMR (acetone-$d_6$); δ [ppm]=1.2 to 2.0 (8H), 3.20 to 4.20 (34H)

Example 4

A compound represented by the aforementioned formula (D) (in the formula (D), bd which indicates the average degree of polymerization is 4.5, and cd which indicates the average degree of polymerization is 4.5) was obtained by a method to be described below.

First, 1,5-cyclononanediol and epibromohydrin were reacted to synthesize a compound represented by the following formula (15).

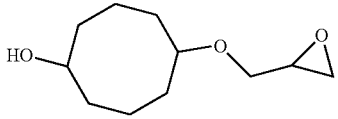

(15)

The same operation as in Example 1 was carried out except that 6.10 g of a compound represented by the formula (15) was used instead of the compound represented by formula (10) used in Example 1, thereby obtaining 11.9 g of the compound represented by the formula (D).

$^1$H-NMR measurement of the obtained compound (D) was carried out, and the structure was identified from the following results.

$^1$H-NMR (acetone-$d_6$); δ [ppm]=1.2 to 2.0 (16H), 3.20 to 4.20 (30H)

Example 5

A compound represented by the aforementioned formula (E) (in the formula (E), be which indicates the average degree of polymerization is 4.5, and ce which indicates the average degree of polymerization is 4.5) was obtained by a method to be described below.

First, 1,6-cyclotridecanediol and epibromohydrin were reacted to synthesize a compound represented by the following formula (16).

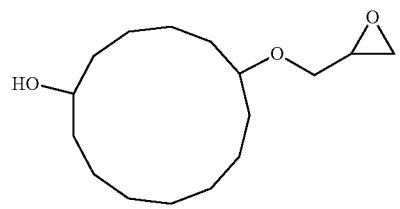

(16)

The same operation as in Example 1 was carried out except that 6.78 g of a compound represented by the formula (16) was used instead of the compound represented by formula (10) used in Example 1, thereby obtaining 12.4 g of the compound represented by the formula (E).

$^1$H-NMR measurement of the obtained compound (E) was carried out, and the structure was identified from the following results.

$^1$H-NMR (acetone-$d_6$); δ [ppm]=1.2 to 2.0 (24H), 3.20 to 4.20 (30H)

Example 6

A compound represented by the aforementioned formula (F) (in the formula (F), bf which indicates the average degree of polymerization is 4.5, and cf which indicates the average degree of polymerization is 4.5) was obtained by a method to be described below.

First, 1,3,5-adamantanetriol and epibromohydrin were reacted to synthesize a compound represented by the following formula (17).

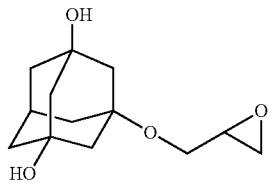

(17)

The same operation as in Example 1 was carried out except that 3.81 g of a compound represented by the formula (17) was used instead of the compound represented by formula (10) used in Example 1, thereby obtaining 12.3 g of the compound represented by the formula (F).

$^1$H-NMR measurement of the obtained compound (F) was carried out, and the structure was identified from the following results.

$^1$H-NMR (acetone-$d_6$); δ [ppm]=1.2 to 2.0 (13H), 3.20 to 4.20 (33H)

Example 7

A compound represented by the aforementioned formula (G) (in the formula (G), bg which indicates the average degree of polymerization is 4.5, and cg which indicates the average degree of polymerization is 4.5) was obtained by a method to be described below.

First, 7-cyclopenta-1-heptene was oxidized to synthesize a compound represented by the following formula (18).

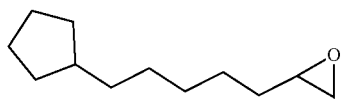
(18)

The same operation as in Example 1 was carried out except that 9.99 g of a compound represented by the formula (18) was used instead of the compound represented by formula (10) used in Example 1, thereby obtaining 12.5 g of the compound represented by the formula (G).

$^1$H-NMR measurement of the obtained compound (G) was carried out, and the structure was identified from the following results.

$^1$H-NMR (acetone-$d_6$); δ [ppm]=1.2 to 2.0 (21H), 3.20 to 4.20 (25H)

Example 8

A compound represented by the aforementioned formula (H) (in the formula (H), bh which indicates the average degree of polymerization is 4.5, and ch which indicates the average degree of polymerization is 4.5) was obtained by a method to be described below.

First, 3-amino-cyclopentan-1-ol and epibromohydrin were reacted to synthesize a compound represented by the following formula (19).

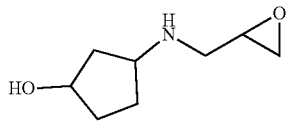
(19)

The same operation as in Example 1 was carried out except that 2.89 g of a compound represented by the formula (19) was used instead of the compound represented by formula (10) used in Example 1, thereby obtaining 11.3 g of the compound represented by the formula (H).

$^1$H-NMR measurement of the obtained compound (H) was carried out, and the structure was identified from the following results.

$^1$H-NMR (acetone-$d_6$); δ [ppm]=1.2 to 2.0 (8H), 3.20 to 4.20 (31H)

Example 9

A compound represented by the aforementioned formula (I) (in the formula (I), bi which indicates the average degree of polymerization is 4.5, and ci which indicates the average degree of polymerization is 4.5) was obtained by a method to be described below.

First, 1-methoxy-cyclopentan-3-ol and epibromohydrin were reacted to synthesize a compound represented by the following formula (20).

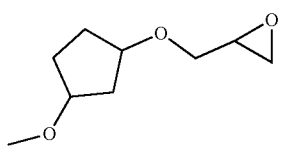
(20)

The same operation as in Example 1 was carried out except that 4.64 g of a compound represented by the formula (20) was used instead of the compound represented by formula (10) used in Example 1, thereby obtaining 12.1 g of the compound represented by the formula (I).

$^1$H-NMR measurement of the obtained compound (I) was carried out, and the structure was identified from the following results.

$^1$H-NMR (acetone-$d_6$); δ [ppm]=1.2 to 2.0 (8H), 3.20 to 4.20 (32H)

Example 10

A compound represented by the aforementioned formula (J) (in the formula (J), bj which indicates the average degree of polymerization is 4.5, and cj which indicates the average degree of polymerization is 4.5) was obtained by a method to be described below.

First, 1-amide-cyclopentan-3-ol and epibromohydrin were reacted to synthesize a compound represented by the following formula (21).

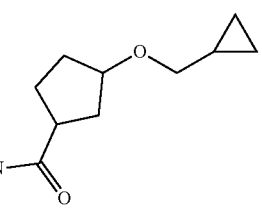
(21)

The same operation as in Example 1 was carried out except that 2.64 g of a compound represented by the formula (21) was used instead of the compound represented by formula (10) used in Example 1, thereby obtaining 10.9 g of the compound represented by the formula (J).

$^1$H-NMR measurement of the obtained compound (J) was carried out, and the structure was identified from the following results.

$^1$H-NMR (acetone-$d_6$); δ [ppm]=1.2 to 2.0 (8H), 2.6 (1H), 3.20 to 4.20 (30H)

Example 11

A compound represented by the aforementioned formula (K) (in the formula (K), bk which indicates the average degree of polymerization is 4.5, and ck which indicates the average degree of polymerization is 4.5) was obtained by a method to be described below.

First, 1-methylamino-cyclopentan-3-ol and epibromohydrin were reacted to synthesize a compound represented by the following formula (22).

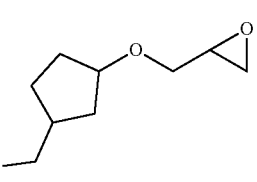
(22)

The same operation as in Example 1 was carried out except that 2.64 g of a compound represented by the formula (22) was used instead of the compound represented by formula (10) used in Example 1, thereby obtaining 10.9 g of the compound represented by the formula (K).

$^1$H-NMR measurement of the obtained compound (K) was carried out, and the structure was identified from the following results.

$^1$H-NMR (acetone-$d_6$); δ [ppm]=1.2 to 2.0 (9H), 3.20 to 4.20 (32H)

Example 12

A compound represented by the aforementioned formula (L) (in the formula (L), bl which indicates the average degree of polymerization is 4.5, and cl which indicates the average degree of polymerization is 4.5) was obtained by a method to be described below.

First, 1-cyano-cyclopentan-3-ol and epibromohydrin were reacted to synthesize a compound represented by the following formula (23).

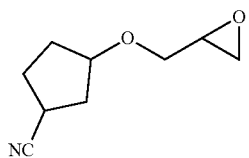

(23)

The same operation as in Example 1 was carried out except that 2.64 g of a compound represented by the formula (23) was used instead of the compound represented by formula (10) used in Example 1, thereby obtaining 10.9 g of the compound represented by the formula (L).

$^1$H-NMR measurement of the obtained compound (L) was carried out, and the structure was identified from the following results.

$^1$H-NMR (acetone-$d_6$); δ [ppm]=1.2 to 2.0 (8H), 2.5 (1H), 3.20 to 4.20 (28H)

Example 13

A compound represented by the aforementioned formula (M) (in the formula (M), bm which indicates the average degree of polymerization is 4.5, and cm which indicates the average degree of polymerization is 4.5) was obtained by a method to be described below.

First, 3-allyloxy-1,2-propanediol-2-methoxymethyl ether and 2-(bromoethoxy)tetrahydro-2H-pyran were reacted, and the product was oxidized to synthesize a compound represented by the following formula (24).

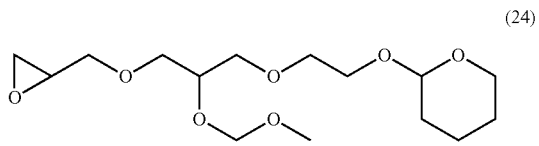 [SMILES: COCOC(COCCOC1CCCCO1)COCC1CO1]

(24)

The same operation as in Example 3 was carried out except that 2.64 g of a compound represented by the formula (24) was used instead of the compound represented by formula (11) used in Example 3, thereby obtaining 10.9 g of the compound represented by the formula (M).

$^1$H-NMR measurement of the obtained compound (M) was carried out, and the structure was identified from the following results.

$^1$H-NMR (acetone-$d_6$); δ [ppm]=1.2 to 2.0 (6H), 3.20 to 4.20 (38H)

Example 14

A compound represented by the aforementioned formula (N) (in the formula (N), bn which indicates the average degree of polymerization is 6.5) was produced by a method to be described below.

The same operation as in Example 13 was carried out except that 40.0 g of a fluoropolyether represented by $HOCH_2CF_2O(CF_2CF_2O)_uCF_2CH_2OH$ (in the formula, u which indicates the average degree of polymerization is 6.5) was used instead of the fluoropolyether represented by $HOCH_2CF_2O(CF_2CF_2O)_s(CF_2O)_tCF_2CH_2OH$ (in the formula, s which indicates the average degree of polymerization is 4.5 and t which indicates the average degree of polymerization is 4.5) used in Example 13, thereby obtaining 10.9 g of the compound represented by the formula (N).

$^1$H-NMR measurement and $^{19}$F-NMR measurement of the obtained compound (N) were carried out, and the structure was identified from the following results.

$^1$H-NMR (acetone-$d_6$); δ [ppm]=1.2 to 2.0 (6H), 3.20 to 4.20 (38H)

$^{19}$F-NMR (acetone-$d_6$): δ [ppm]=−77.85 to −79.00 (4F), −88.50 to −91.22 (26F)

Example 15

A compound represented by the aforementioned formula (O) (in the formula (O), eo which indicates the average degree of polymerization is 4.5) was produced by a method to be described below.

The same operation as in Example 13 was carried out except that 40.0 g of a fluoropolyether represented by $HOCH_2CF_2CF_2O(CF_2CF_2CF_2O)_vCF_2CF_2CH_2OH$ (in the formula, v which indicates the average degree of polymerization is 4.5) was used instead of the fluoropolyether represented by $HOCH_2CF_2O(CF_2CF_2O)_s(CF_2O)_tCF_2CH_2OH$ (in the formula, s which indicates the average degree of polymerization is 4.5 and t which indicates the average degree of polymerization is 4.5) used in Example 13, thereby obtaining 10.7 g of the compound represented by the formula (O).

$^1$H-NMR measurement and $^{19}$F-NMR measurement of the obtained compound (O) were carried out, and the structure was identified from the following results.

$^1$H-NMR (acetone-$d_6$); δ [ppm]=1.2 to 2.0 (6H), 3.20 to 4.20 (38H)

$^{19}$F-NMR (acetone-$d_6$): δ [ppm]=−82.66 to −84.00 (20F), −85.16 to −86.91 (4F), −123.16 to −124.91 (4F), −128.47 to −130.20 (4F)

Example 16

A compound represented by the aforementioned formula (T) (in the formula (T), bt which indicates the average degree of polymerization is 4.5, and ct which indicates the average degree of polymerization is 4.5.) was obtained by a method to be described below.

First, 1,2-cyclopentanediol, epibromohydrin and 2-(bromopropoxy)tetrahydro-2H-pyran were reacted to synthesize a compound represented by the following formula (28).

(28)

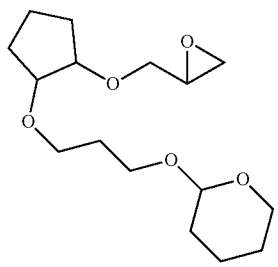

The same operation as in Example 1 was carried out except that 5.90 g of a compound represented by the formula (28) was used instead of the compound represented by formula (10) used in Example 1, thereby obtaining 11.9 g of the compound represented by the formula (T).

$^1$H-NMR measurement of the obtained compound (T) was carried out, and the structure was identified from the following results.

$^1$H-NMR (acetone-$d_6$); δ [ppm]=1.2 to 2.0 (10H), 3.20 to 4.20 (34H)

Example 17

A compound represented by the aforementioned formula (U) (in the formula (U), bu which indicates the average degree of polymerization is 4.5, and cu which indicates the average degree of polymerization is 4.5.) was obtained by a method to be described below.

First, 1,3,5-cyclohexanetriol, t-butyldimethylchlorosilane, epibromohydrin, and 2-(bromoethoxy)tetrahydro-2H-pyran were reacted to synthesize a compound represented by the following formula (29).

(29)

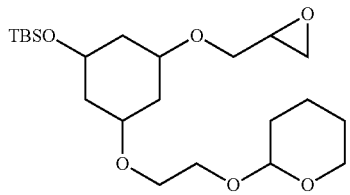

(In the formula (29), TBS represents a t-butyldimethylsilyl group.)

The same operation as in Example 1 was carried out except that 7.20 g of a compound represented by the formula (29) was used instead of the compound represented by formula (10) used in Example 1, thereby obtaining 10.8 g of the compound represented by the formula (U).

$^1$H-NMR measurement of the obtained compound (U) was carried out, and the structure was identified from the following results.

$^1$H-NMR (acetone-$d_6$); δ [ppm]=1.2 to 2.0 (8H), 3.20 to 4.20 (36H)

Example 18

A compound represented by the aforementioned formula (V) (in the formula (V), by which indicates the average degree of polymerization is 4.5, and cv which indicates the average degree of polymerization is 4.5.) was obtained by a method to be described below.

First, 1,3,5-cyclohexanetriol, t-butyldimethylchlorosilane, epibromohydrin, and 2-(bromopropoxy)tetrahydro-2H-pyran were reacted to synthesize a compound represented by the following formula (30).

(30)

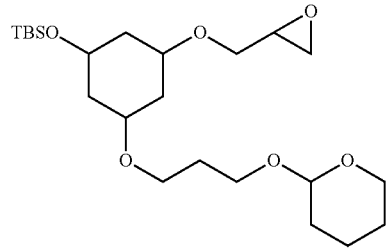

(In the formula, TBS represents a t-butyldimethylsilyl group.)

The same operation as in Example 1 was carried out except that 7.50 g of a compound represented by the formula (30) was used instead of the compound represented by formula (10) used in Example 1, thereby obtaining 10.4 g of the compound represented by the formula (V).

$^1$H-NMR measurement of the obtained compound (V) was carried out, and the structure was identified from the following results.

$^1$H-NMR (acetone-$d_6$); δ [ppm]=1.2 to 2.0 (10H), 3.20 to 4.20 (36H)

Example 19

A compound represented by the aforementioned formula (W) (in the formula (W), bw which indicates the average degree of polymerization is 4.5, and cw which indicates the average degree of polymerization is 4.5.) was obtained by a method to be described below.

First, 1,3,5-cyclohexanetriol, epibromohydrin and 2-(bromoethoxy)tetrahydro-2H-pyran were reacted to synthesize a compound represented by the following formula (31).

(31)

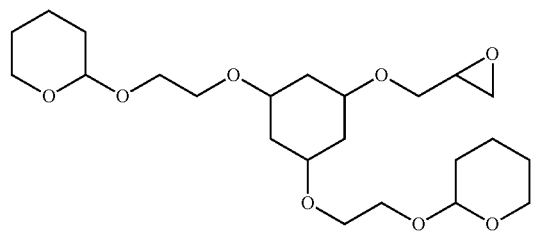

The same operation as in Example 1 was carried out except that 6.50 g of a compound represented by the formula (31) was used instead of the compound represented by formula (10) used in Example 1, thereby obtaining 9.5 g of the compound represented by the formula (W).

$^1$H-NMR measurement of the obtained compound (W) was carried out, and the structure was identified from the following results.

$^1$H-NMR (acetone-$d_6$); δ [ppm]=1.2 to 2.0 (8H), 3.20 to 4.20 (40H)

Example 20

A compound represented by the aforementioned formula (X) (in the formula (X), bx which indicates the average degree of polymerization is 4.5, and cx which indicates the average degree of polymerization is 4.5.) was obtained by a method to be described below.

First, 1,3,5-cyclohexanetriol, epibromohydrin and 2-(bromopropoxy)tetrahydro-2H-pyran were reacted to synthesize a compound represented by the following formula (32).

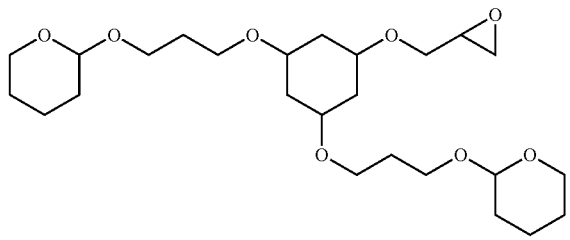

(32)

The same operation as in Example 1 was carried out except that 5.50 g of a compound represented by the formula (32) was used instead of the compound represented by formula (10) used in Example 1, thereby obtaining 8.4 g of the compound represented by the formula (X).

$^1$H-NMR measurement of the obtained compound (X) was carried out, and the structure was identified from the following results.

$^1$H-NMR (acetone-$d_6$); δ [ppm]=1.2 to 2.0 (12H), 3.20 to 4.20 (40H)

Comparative Example 1

A compound represented by the following formula (P) was obtained by the method described below.

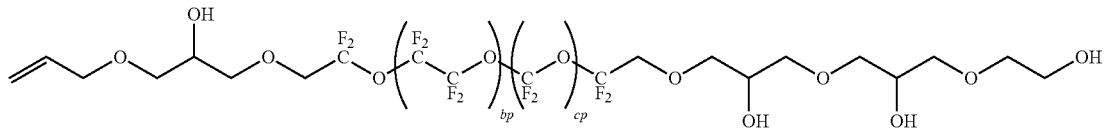

(P)

(In the formula (P), bp which indicates the average degree of polymerization was 4.5 and cp which indicates the average degree of polymerization was 4.5.)

First, the compound represented by the following formula (25) was synthesized by reacting allyl alcohol and epibromohydrin.

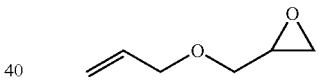

(25)

Then, the same operation as in Example 13 was carried out except that 2.64 g of a compound represented by the formula (25) was used instead of the compound represented by formula (14) used in Example 13, thereby obtaining 10.9 g of the compound represented by the formula (P).

$^1$H-NMR measurement of the obtained compound (P) was carried out, and the structure was identified from the following results.

$^1$H-NMR (acetone-$d_6$); δ [ppm]=3.20 to 4.20 (29H), 5.00 to 6.00 (3H)

Comparative Example 2

A compound represented by the following formula (Q) was obtained by the method described below.

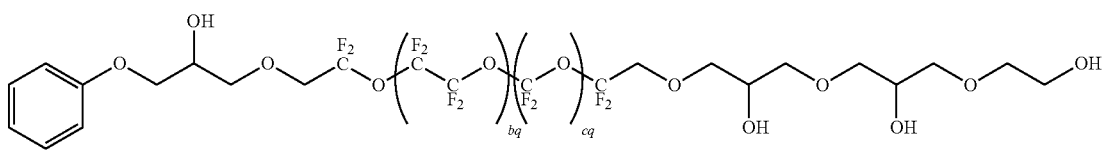

(Q)

(In the formula (Q), bq which indicates the average degree of polymerization was 4.5 and cq which indicates the average degree of polymerization was 4.5.)

First, the compound represented by the following formula (26) was synthesized by reacting phenol and epibromohydrin.

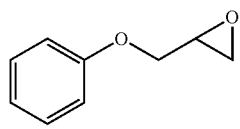
(26)

Then, the same operation as in Example 13 was carried out except that 2.64 g of a compound represented by the formula (26) was used instead of the compound represented by formula (14) used in Example 13, thereby obtaining 10.9 g of the compound represented by the formula (Q).

$^1$H-NMR measurement of the obtained compound (Q) was carried out, and the structure was identified from the following results.

$^1$H-NMR (acetone-$d_6$); δ [ppm]=3.20 to 4.20 (27H), 6.6 to 7.4 (5H)

Comparative Example 3

A compound represented by the following formula (R) was obtained by the method described below.

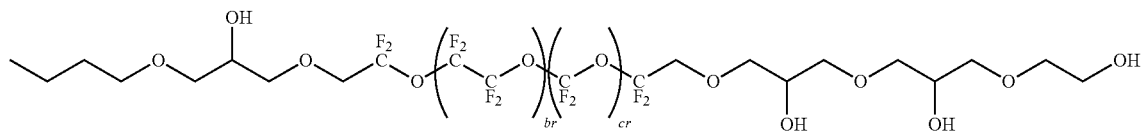
(R)

(In the formula (R), br which indicates the average degree of polymerization was 4.5 and cr which indicates the average degree of polymerization was 4.5.)

First, the compound represented by the following formula (27) was synthesized by reacting 1-butanol and epibromohydrin.

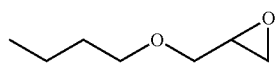
(27)

The same operation as in Example 13 was carried out except that 2.64 g of a compound represented by the formula (27) was used instead of the compound represented by formula (14) used in Example 13, thereby obtaining 10.9 g of the compound represented by the formula (R).

$^1$H-NMR measurement of the obtained compound (R) was carried out, and the structure was identified from the following results.

$^1$H-NMR (acetone-$d_6$); δ [ppm]=1.2 to 2.0 (7H), 3.20 to 4.20 (29H)

Comparative Example 4

A compound represented by the following formula (S) was obtained by the method described below.

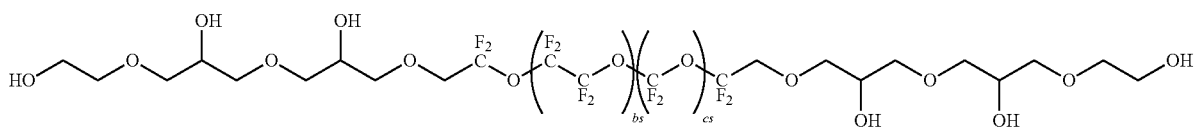
(S)

(In the formula (S), bs which indicates the average degree of polymerization was 4.5 and cs which indicates the average degree of polymerization was 4.5.)

The same operation as in Example 13 was carried out except that 2.64 g of a compound represented by the formula (24) was used instead of the compound represented by formula (14) used in Example 13, thereby obtaining 10.9 g of the compound represented by the formula (S).

$^1$H-NMR measurement of the obtained compound (S) was carried out, and the structure was identified from the following results.

$^1$H-NMR (acetone-$d_6$); δ [ppm]=3.20 to 4.20 (38H)

The number-average molecular weights of the compounds of Examples 1 to 20 and Comparative Examples 1 to 4 obtained as described above were obtained by the aforementioned $^1$H-NMR and $^{19}$F-NMR measurements. The results are shown in Table 1. It is assumed that, in the values of the average molecular weight of the synthesized compounds, variations of approximately 1 to 5 may exist depending on the molecular weight distributions of the fluoropolyether used as a raw material of the compounds, differences in the operation at the time of synthesizing the compounds and the like.

"Heat Resistance Evaluation"

A (Favorable): Thermal decomposition temperature is 250° C. or more.

B (Permissible): Thermal decomposition temperature is 100° C. or more and less than 250° C.

C (Impermissible): Thermal decomposition temperature is less than 100° C.

Next, solutions for forming a lubricating layer were prepared using the compounds obtained in Examples 1 to 20 and Comparative Examples 1 to 4 by a method described below. Then, lubricating layers of magnetic recording media were formed using the obtained solutions for forming a lubricating layer by a method to be described below, and magnetic recording media of Examples 1 to 20 and Comparative Examples 1 to 4 were obtained.

"Solutions for Forming Lubricating Layer"

The compounds obtained in Examples 1 to 20 and Comparative Examples 1 to 4 were respectively dissolved in VERTREL (registered trademark) XF (trade name, manufactured by Dupont-Mitsui Fluorochemicals Co., Ltd.), which is a fluorine-based solvent, and diluted with VERTREL XF, so that the film thicknesses became 9 Å to 10 Å

TABLE 1

| | Compound | Number-average molecular weight | Film thickness (Å) | Heat resistance test | Amount of Si adsorbed | Pickup Suppression Test | Comprehensive evaluation |
|---|---|---|---|---|---|---|---|
| Example 1 | (A) | 1336 | 9.0 | A | 0.45 | AA | A |
| Example 2 | (B) | 1378 | 9.5 | A | 0.46 | AA | A |
| Example 3 | (C) | 1449 | 9.5 | A | 0.32 | AA | A |
| Example 4 | (D) | 1421 | 9.5 | A | 0.39 | AA | A |
| Example 5 | (E) | 1477 | 10.0 | A | 0.48 | AA | A |
| Example 6 | (F) | 1447 | 9.5 | A | 0.52 | AA | A |
| Example 7 | (G) | 1389 | 9.5 | A | 0.55 | AA | A |
| Example 8 | (H) | 1363 | 10.0 | A | 0.52 | AA | A |
| Example 9 | (I) | 1378 | 9.5 | A | 0.36 | AA | A |
| Example 10 | (J) | 1391 | 10.0 | A | 0.41 | AA | A |
| Example 11 | (K) | 1377 | 10.0 | A | 0.37 | AA | A |
| Example 12 | (L) | 1373 | 9.5 | A | 0.35 | AA | A |
| Example 13 | (M) | 1439 | 9.5 | A | 0.33 | AA | A |
| Example 14 | (N) | 1339 | 9.5 | A | 0.37 | AA | A |
| Example 15 | (O) | 1439 | 10.0 | A | 0.35 | AA | A |
| Example 16 | (T) | 1463 | 9.5 | A | 0.33 | AA | A |
| Example 17 | (U) | 1479 | 10.0 | A | 0.38 | AA | A |
| Example 18 | (V) | 1493 | 10.0 | A | 0.37 | AA | A |
| Example 19 | (W) | 1523 | 9.5 | A | 0.35 | AA | A |
| Example 20 | (X) | 1551 | 10.0 | A | 0.34 | AA | A |
| Comparative Example 1 | (P) | 1306 | 10.0 | C | 1.00 | A | C |
| Comparative Example 2 | (Q) | 1342 | 9.5 | A | 0.41 | C | C |
| Comparative Example 3 | (R) | 1322 | 10.0 | A | 0.83 | A | C |
| Comparative Example 4 | (S) | 1384 | 10.0 | A | 0.85 | AA | C |

(Heat Resistance Test)

Heat resistance tests of the compounds of Examples 1 to 20 and Comparative Examples 1 to 4 were carried out and evaluated by conducting the method described below. Weight reduction with respect to temperature rising was measured regarding each compound with TG-DTA (manufacturer name: Seiko Instruments Inc., model number; EXSTAR 6000), and a temperature at which the weight of the compound decreased by 5% was defined as a thermal decomposition temperature. As measurement conditions, a temperature rising rate was set to 10° C./min and an air flow rate was set to 200 mL/min. The results are shown in Table 1.

when applied onto a protective layer, and they were used as solutions for forming a lubricating layer.

"Magnetic Recording Media"

Magnetic recording media having an adhesive layer, a soft magnetic layer, a first underlayer, a second underlayer, a magnetic layer and a protective layer which were sequentially provided on a substrate having a diameter of 65 mm were prepared. As the protective layer, a carbon layer was used.

The solutions for forming a lubricating layer of Examples 1 to 20 and Comparative Examples 1 to 4 were applied by the dipping method onto the protective layers of the magnetic recording media in which the individual layers up to the protective layer had been formed. The dipping method was carried out under conditions of an immersion speed of 10 mm/sec, an immersion time of 30 seconds and a lifting speed of 1.2 mm/sec.

After that, the magnetic recording media to which the solutions for forming a lubricating layer had been applied were put into a thermostatic chamber of 120° C. and heated for 10 minutes to remove the solvent in the solutions for forming a lubricating layer, thereby forming lubricating layers on the protective layers and obtaining magnetic recording media.

(Film Thickness Measurement)

The film thicknesses of the lubricating layers in the magnetic recording media of Examples 1 to 20 and Comparative Examples 1 to 4 obtained as described above were measured using FT-IR (trade name: Nicolet iS50, manufactured by Thermo Fisher Scientific). The results are shown in Table 1.

In addition, a chemical substance resistance test and a pickup suppression test were carried out as described below on the magnetic recording media of Examples 1 to 20 and Comparative Examples 1 to 4. The results are shown in Table 1.

(Chemical Substance Resistance Test)

Contamination of the magnetic recording media due to an environmental substance that generates a contamination substance in a high-temperature environment was inspected by an evaluation method to be described below. In the evaluation method to be described below, Si ions were used as the environmental substance, and the amount of Si adsorbed was measured as the amount of the contamination substance that was generated by the environmental substance and contaminated the magnetic recording media.

Specifically, the magnetic recording medium, which was an evaluation subject, was held under a high-temperature environment of 85° C. and a humidity of 0% in the presence of siloxane-based Si rubber for 240 hours. Next, the adsorbed amount of Si present on the surface of the magnetic recording medium was analyzed and measured using secondary-ion mass spectrometry (SIMS), and the degree of contamination by Si ions was evaluated as the amount of Si adsorbed. The evaluation of the amount of Si adsorbed was evaluated using a numerical value relative to the result of Comparative Example 1 which was regarded as 1.00. The results are shown in Table 1. As the numerical value becomes smaller, the chemical substance resistance becomes superior.

(Pickup Suppression Test)

The magnetic recording media and a magnetic head were mounted on a spin stand, and the magnetic head was floated at a fixed point for 10 minutes under normal temperature and reduced pressure conditions (about 250 torr), while the magnetic recording medium was rotating. Subsequently, the surface of the magnetic head facing the magnetic recording medium (the surface of the lubricating layer) was analyzed using an Electron Spectroscopy for Chemical Analysis (ESCA) analyzer. Based on the intensity of the fluorine-derived peak (signal intensity (a.u.)) measured by ESCA, the amount of the lubricant adhered to the magnetic head was evaluated using the criteria shown below.

"Evaluation of Pickup Suppression Test"

AA (Excellent): ESCA signal intensity is 500 or less, and therefore it is very small. (The adhesion of lubricant to the head is very small.)

A (Favorable): ESCA signal intensity is 501 or more and 1000 or less, and therefore it is small. (The adhesion of lubricant to the head is small.)

C (Impermissible): ESCA signal intensity is 1001 or more, and therefore it is large. (The adhesion of lubricant to the head is large.)

In addition, the compounds and the magnetic recording media of Examples 1 to 20 and Comparative Examples 1 to 4 were comprehensively evaluated based on criteria to be described below. The results are shown in Table 1.

(Comprehensive Evaluation)

A (Favorable): The heat resistance evaluation is A, the amount of Si adsorbed is 0.60 or less, and the evaluation of pickup suppression test is AA (excellent) or A (favorable).

C (Impermissible): The criteria of A (favorable) of comprehensive evaluation is not fulfilled.

As shown in Table 1, in Examples 1 to 20, all results of the heat resistance test, the chemical substance resistance test (amount of Si adsorbed) and the pickup suppression test thereof were favorable, and therefore the comprehensive evaluation thereof was A (favorable).

On the other hand, in Comparative Examples 1 to 4, when the results of the heat resistance test, the chemical substance resistance test (amount of Si adsorbed) and the pickup suppression test thereof were totally evaluated, the results thereof were poor as compared with that of Examples 1 to 20, and the comprehensive evaluation thereof was C (Impermissible).

More specifically, in Comparative Example 1 using the compound (P) which includes a chain structure having a double bond instead of an organic group represented by $R^1$ in the formula (1), the evaluation of the heat resistance test was C, and the result of the chemical substance resistance test thereof was poor.

Furthermore, in Comparative Example 2 using the compound (Q) which includes a benzene ring instead of an organic group represented by $R^1$ in the formula (1), the evaluation of the pickup suppression test was C (impermissible).

Furthermore, in Comparative Example 3 using the compound (R) which includes a straight-chain alkyl group instead of an organic group represented by $R^1$ in the formula (1), the result of the chemical substance resistance test was poor.

Furthermore, in Comparative Example 4 using the compound (S) which includes a straight-chain alkyl group, in which the terminal is substituted by a hydroxyl group, instead of an organic group represented by $R^1$ in the formula (1), the result of the chemical substance resistance test was poor.

From these facts, it was found that lubricating layers which exhibit excellent chemical substance resistance and excellent heat resistance, and hardly generate pickup even when the thickness thereof is reduced to 9 Å to 10 Å, can be obtained by forming the lubricating layers which contain the compounds of Examples 1 to 20 on the protective layers of the magnetic recording media.

INDUSTRIAL APPLICABILITY

The present invention provides a fluorine-containing ether compound capable of forming a lubricating layer which has excellent chemical substance resistance and heat resistance and suppresses pickup in spite of a thin thickness.

When a lubricant for a magnetic recording medium which contains the fluorine-containing ether compound of the present invention is used, a lubricating layer which has excellent heat resistance and chemical substance resistance and can suppress pickup in spite of a thin thickness can be obtained.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by the following formula (1), $$R^1-R^2-CH_2-R^3-CH_2-R^4 \quad (1)$$

(in the formula (1), $R^1$ is an organic group having an alicyclic structure having 3 to 13 carbon atoms; $R^2$ is represented by the following formula (2), and a in the formula (2) is an integer of 1 to 3; $R^3$ is a perfluoropolyether chain; and $R^4$ is a terminal group having two or three polar groups, in which individual polar groups bond to different carbon atoms and the carbon atoms to which the polar groups bond are bonded to each other through a linking group having a carbon atom to which the polar groups do not bond).

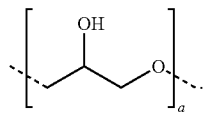
(2)

2. The fluorine-containing ether compound according to claim 1,
wherein the alicyclic structure of $R^1$ is a saturated alicyclic structure.

3. The fluorine-containing ether compound according to claim 1,
wherein the alicyclic structure of $R^1$ is one selected from the group consisting of cyclopropane, cyclobutane, cyclopentane, cyclohexane, cycloheptane, cyclooctane, cyclononane, cyclodecane, cycloundecane, cyclododecane, cyclotridecane and adamantane.

4. The fluorine-containing ether compound according to Claim 1,
wherein any one of a carbon atom, an oxygen atom and a nitrogen atom included in $R^1$ is bonded to a carbon atom included in $R^2$.

5. The fluorine-containing ether compound according to claim 1,
wherein the alicyclic structure of $R^1$ has a substituent, which is selected from a functional group selected from the group consisting of a hydroxyl group, an alkoxy group, an amide group, an amino group, a carbonyl group, a carboxyl group, a nitro group, a cyano group and a sulfo group, or an alkyl group having the functional group.

6. The fluorine-containing ether compound according to Claim 1,
wherein $R^3$ is any of the following formulae (3) to (5), $$-CF_2O-(CF_2CF_2O)_b-(CF_2O)_c-CF_2- \quad (3)$$

(b and c in the formula (3) indicate average degrees of polymerization and each independently represents 0 to 30; here, there is no case where b and c become 0 at the same time)

$$-CF(CF_3)-(OCF(CF_3)CF_2)_d-OCF(CF_3)- \quad (4)$$

(d in the formula (4) indicates an average degree of polymerization and represents 0.1 to 30)

$$-CF_2CF_2O-(CF_2CF_2CF_2O)_e-CF_2CF_2- \quad (5)$$

(e in the formula (5) indicates an average degree of polymerization and represents 0.1 to 30).

7. The fluorine-containing ether compound according to Claim 1,
wherein the polar group in $R^4$ is a hydroxyl group.

8. The fluorine-containing ether compound according to Claim 1,
wherein $R^4$ is a terminal group which is any of the following formulae (6) to (9)

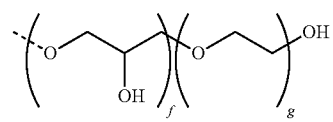
(6)

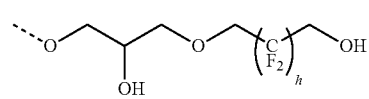
(7)

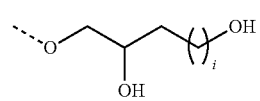
(8)

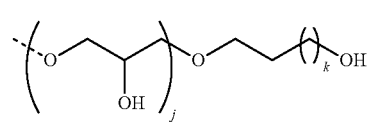
(9)

(In the formula (6), f represents an integer of 1 or 2, and g represents an integer of 1 to 5)
(in the formula (7), h represents an integer of 2 to 5)
(in the formula (8), i represents an integer of 1 to 5)
(in the formula (9), j represents an integer of 1 or 2, and k represents an integer of 1 or 2).

9. The fluorine-containing ether compound according to Claim 1,
wherein a number-average molecular weight thereof is within a range of 500 to 10000.

10. The fluorine-containing ether compound according to Claim 1,
wherein the compound represented by the formula (1) is any of compounds represented by the following formulae (A) to (C), and (G) to (O)

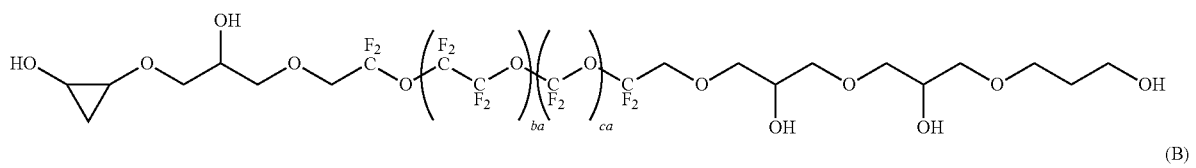

(A)

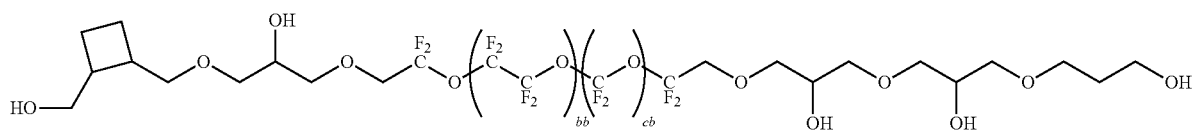

(B)

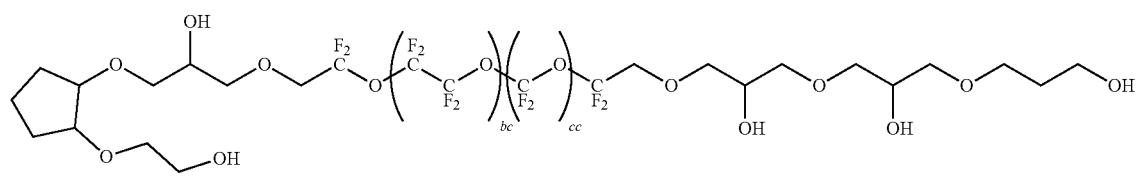

(C)

(in the formula (A), ba and ca indicate average degrees of polymerization, ba represents 0 to 30, and ca represents 0 to 30; here, there is no case where ba and ca become 0 at the same time)

(in the formula (B), bb and cb indicate average degrees of polymerization, bb represents 0 to 30, and cb represents 0 to 30; here, there is no case where bb and cb become 0 at the same time)

(in the formula (C), bc and cc indicate average degrees of polymerization, bc represents 0 to 30, and cc represents 0 to 30; here, there is no case where bc and cc become 0 at the same time)

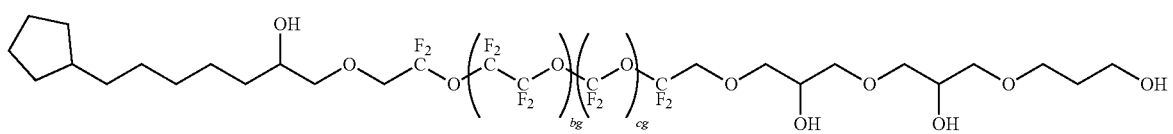

(G)

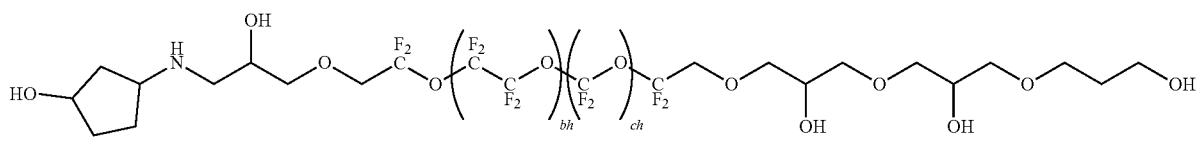

(H)

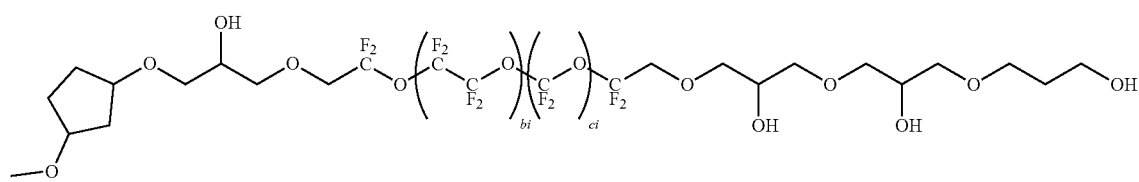

(I)

(in the formula (G), bg and cg indicate average degrees of polymerization, bg represents 0 to 30, and cg represents 0 to 30; here, there is no case where bg and cg become 0 at the same time)

(in the formula (H), bh and ch indicate average degrees of polymerization, bh represents 0 to 30, and ch represents 0 to 30; here, there is no case where bh and ch become 0 at the same time)

(in the formula (I), bi and ci indicate average degrees of polymerization, bi represents 0 to 30, and ci represents 0 to 30; here, there is no case where bi and ci become 0 at the same time)

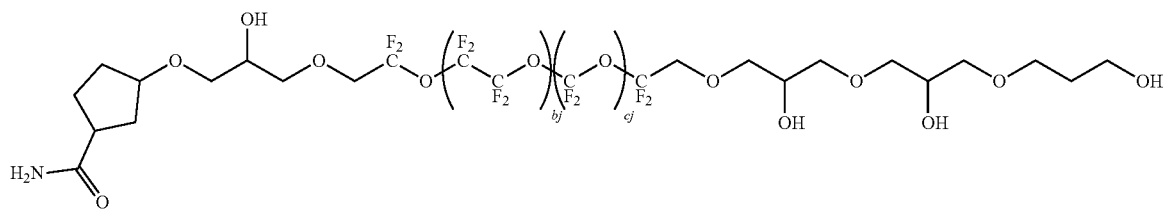

(J)

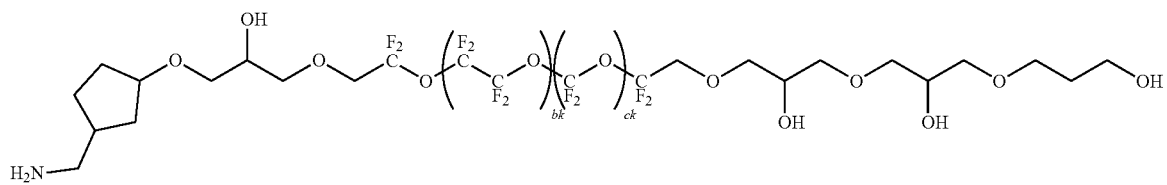

(K)

(in the formula (J), bj and cj indicate average degrees of polymerization, bj represents 0 to 30, and cj represents 0 to 30; here, there is no case where bj and cj become 0 at the same time)

(in the formula (K), bk and ck indicate average degrees of polymerization, bk represents 0 to 30, and ck represents 0 to 30; here, there is no case where bk and ck become 0 at the same time)

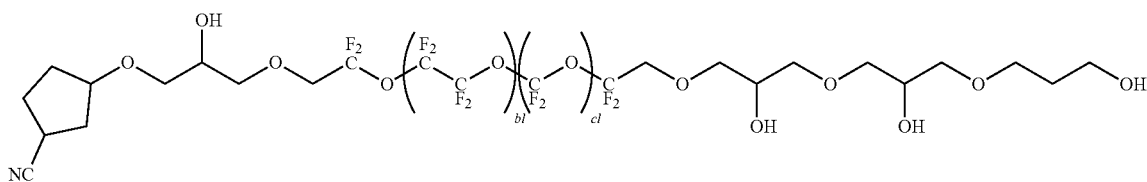

(L)

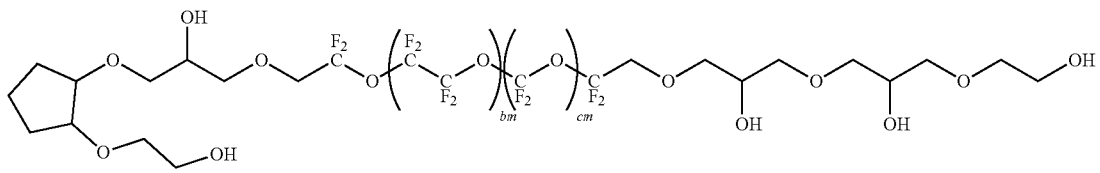

(M)

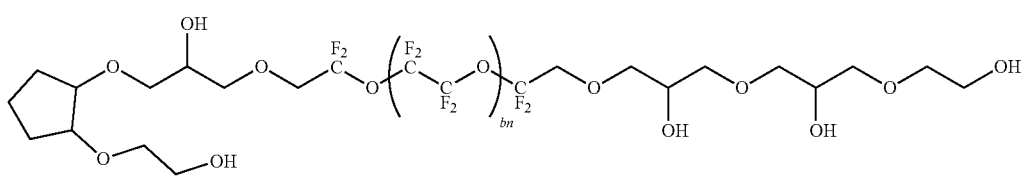

(N)

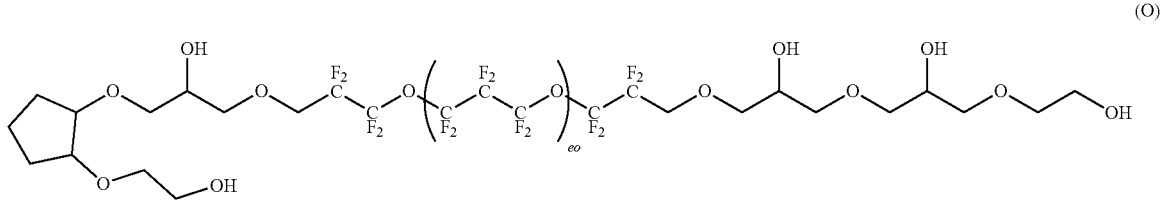

(O)

(in the formula (L), bl and cl indicate average degrees of polymerization, bl represents 0 to 30, and cl represents 0 to 30; here, there is no case where bl and cl become 0 at the same time)

(in the formula (M), bm and cm indicate average degrees of polymerization, bm represents 0 to 30, and cm represents 0 to 30; here, there is no case where bm and cm become 0 at the same time)

(in the formula (N), bn indicates an average degree of polymerization, and bn represents 0.1 to 30)

(in the formula (O), eo indicates an average degree of polymerization, and eo represents 0.1 to 30).

11. The fluorine-containing ether compound according to Claim 1,
wherein the compound represented by the formula (1) is any of compounds represented by the following formulae (T) to (X)

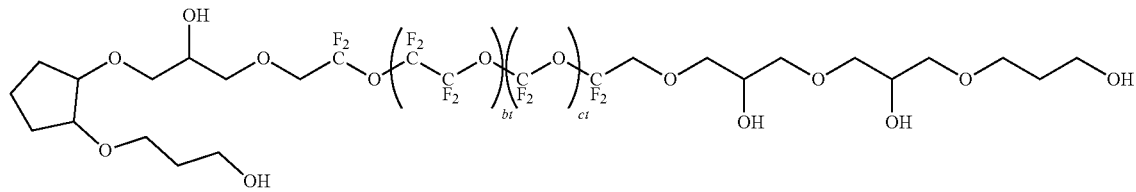

(T)

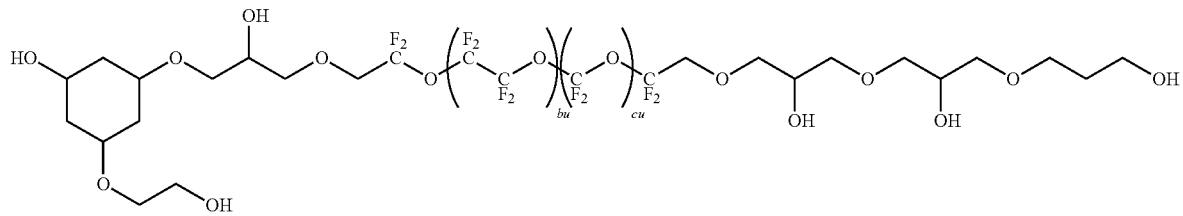

(U)

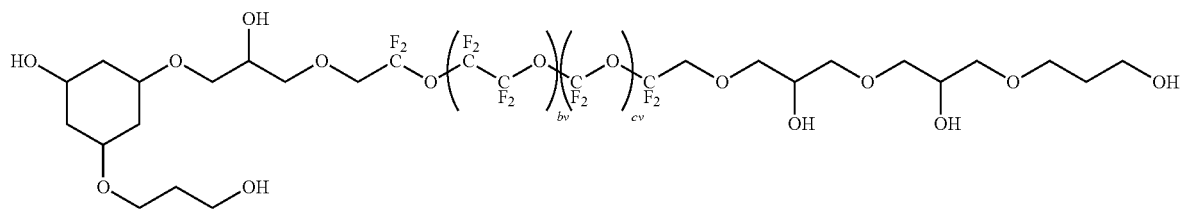

(V)

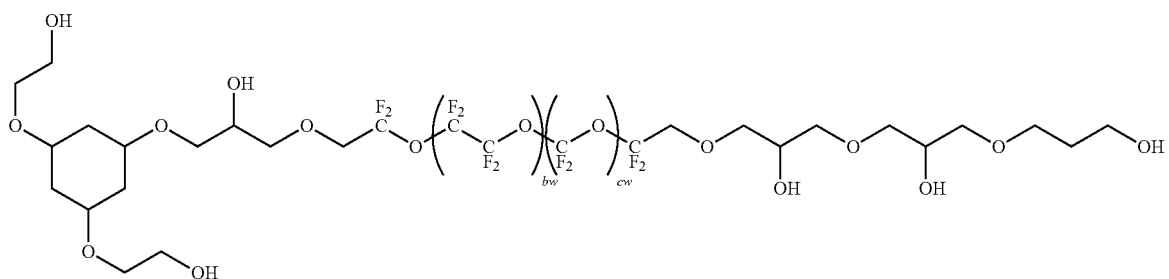

(W)

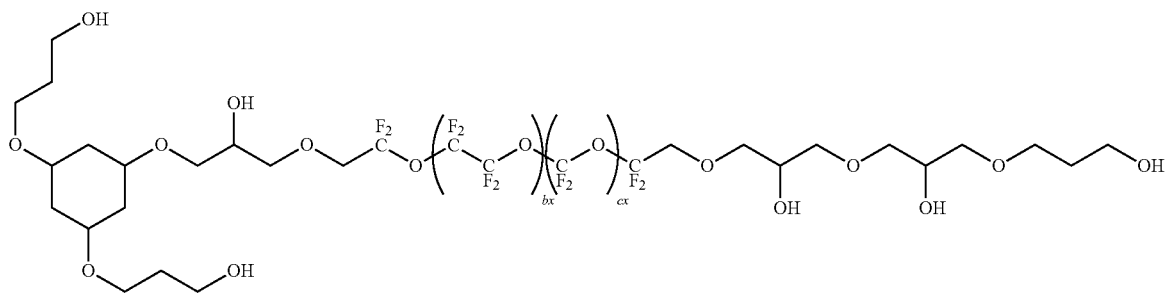

(X)

(in the formula (T), bt and ct indicate average degrees of polymerization, bt represents 0 to 30, and ct represents 0 to 30; here, there is no case where bt and ct become 0 at the same time)

(in the formula (U), bu and cu indicate average degrees of polymerization, bu represents 0 to 30, and cu represents 0 to 30; here, there is no case where bu and cu become 0 at the same time)

(in the formula (V), bv and cv indicate average degrees of polymerization, bv represents 0 to 30, and cv represents 0 to 30; here, there is no case where bv and cv become 0 at the same time)

(in the formula (W), bw and cw indicate average degrees of polymerization, bw represents 0 to 30, and cw represents 0 to 30; here, there is no case where bw and cw become 0 at the same time)

(in the formula (X), bx and cx indicate average degrees of polymerization, bx represents 0 to 30, and cx represents 0 to 30; here, there is no case where bx and cx become 0 at the same time).

12. A lubricant for a magnetic recording medium, comprising:

the fluorine-containing ether compound according to Claim 1.

13. A magnetic recording medium comprising at least:

a magnetic layer;

a protective layer; and a lubricating layer sequentially provided on a substrate, wherein the lubricating layer contains the fluorine-containing ether compound according to Claim 1.

14. The magnetic recording medium according to claim 13, wherein the lubricating layer has an average film thickness of 0.5 nm to 2 nm.

* * * * *